United States Patent
Bleicher et al.

(10) Patent No.: US 11,091,514 B2
(45) Date of Patent: Aug. 17, 2021

(54) PEPTIDE MACROCYCLES AND USE THEREOF IN THE TREATMENT OF BACTERIAL INFECTIONS

(71) Applicant: Hoffmann-La Roche Inc., Little Falls, NJ (US)

(72) Inventors: Konrad Bleicher, Basel (CH); Jérôme Hert, Basel (CH); Carsten Kroll, Basel (CH); Fabian Dey, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/596,243

(22) Filed: Oct. 8, 2019

(65) Prior Publication Data
US 2020/0040032 A1 Feb. 6, 2020

Related U.S. Application Data

(63) Continuation of application No. PCT/EP2018/058954, filed on Apr. 9, 2018.

(30) Foreign Application Priority Data

Apr. 10, 2017 (EP) .................................... 17165654

(51) Int. Cl.
*C07K 5/09* (2006.01)
*A61P 31/04* (2006.01)
*A61K 38/00* (2006.01)

(52) U.S. Cl.
CPC ............ *C07K 5/0815* (2013.01); *A61P 31/04* (2018.01); *A61K 38/00* (2013.01)

(58) Field of Classification Search
None
See application file for complete search history.

(56) References Cited

FOREIGN PATENT DOCUMENTS

| CN | 105669519 A | 6/2016 | |
| WO | WO-2005118613 A2 * | 12/2005 | ........... C07K 5/0812 |
| WO | WO-2012036907 A2 * | 3/2012 | ............. C07K 9/001 |

OTHER PUBLICATIONS

Meyer et al. "Biaryl-Bridged Macrocyclic Peptides: Conformational Constraint via Carbogenic Fusion of Natural Amino Acid Side Chains," J. Org. Chem. 2012, 77, 3099-3114 (Year: 2012).*
PCT International Search Report and Written Opinion for PCT/EP2018/058954, dated Jun. 18, 2018, 11 pages.
PCT International Preliminary Report on Patentability (IPRP) for PCT/EP2018/058954, dated Oct. 15, 2019, 6 pages.

* cited by examiner

*Primary Examiner* — Christina Bradley
(74) *Attorney, Agent, or Firm* — Andre T. Krammer

(57) ABSTRACT

The present invention provides compounds of formula (I)

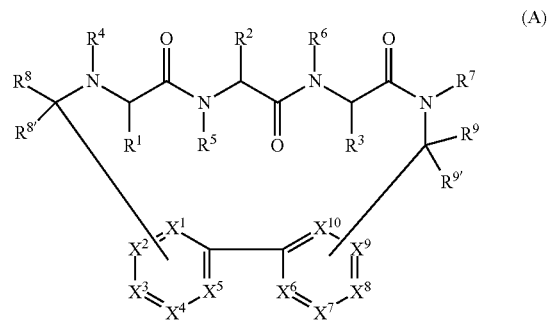

wherein $R^1$, $R^2$, $R^3$, $R^4$, $R^5$, $R^6$, $R^7$, $R^8$, $R^{8'}$, $R^9$, $R^{9'}$, $X^1$, $X^2$, $X^3$, $X^4$, $X^5$, $X^6$, $X^7$, $X^8$, $X^9$ and $X^{10}$ are as described herein, as well as pharmaceutically acceptable salts thereof. Further the present invention is concerned with the manufacture of the compounds of formula (I), pharmaceutical compositions comprising them and their use as medicaments for the treatment of diseases and infections caused by *Acinetobacter baurnannii*.

11 Claims, No Drawings

PEPTIDE MACROCYCLES AND USE THEREOF IN THE TREATMENT OF BACTERIAL INFECTIONS

CROSS-REFERENCE TO RELATED APPLICATIONS

This application is a continuation of International Application No. PCT/EP2018/058954, filed Apr. 9, 2018, which claims benefit of priority to EP Application No. 17165654.9, filed Apr. 10, 2017, each of which are incorporated herein by reference in its entirety.

INTRODUCTION

The present invention provides compounds which exhibit activity against *Acinetobacter baumannii*, their manufacture, pharmaceutical compositions comprising them and their use as medicaments for the treatment of diseases and infections caused by *Acinetobacter baumannii*.

In particular, the present invention relates to compounds of formula (A)

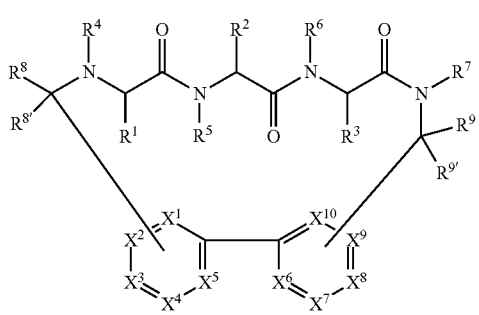

wherein $R^1$, $R^2$, $R^3$, $R^4$, $R^5$, $R^6$, $R^7$, $R^8$, $R^{8'}$, $R^9$, $R^{9'}$, $X^1$, $X^2$, $X^3$, $X^4$, $X^5$, $X^6$, $X^7$, $X^8$, $X^9$ and $X^{10}$ are as described herein, and pharmaceutically acceptable salts thereof.

BACKGROUND

*Acinetobacter baumannii* is a Gram-negative, aerobic, nonfermenting bacterium recognized over the last decades as an emergining pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinates and shows an environmental persistance that allows its survival and spread in the nosocomial setting, making this organism a frequent cause of outbreaks of infection and an endemic, health careassociated pathogen.

Due to increasing antibiotic resistance to most if not all available therapeutic options, Multi-Drug Resistant (MDR) *A. baumannii* infections, especially those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii*.

The present invention provides a novel chemotype (peptide macrocycles) that exhibits activity against drug-susceptible as well as drug-resistant strains of *Acinetobacter baumannii*.

The molecules have been routinely tested against drug susceptible *A. baumannii* strains (ATCC19606 and ATCC 17978) and in addition over a panel of ten clinical isolates. Some representative molecules were selected for in vivo profiling. Both, the pharmacokinetic profile as well as the efficacy in a mouse septicemia model are indicative of a great potential for further development of the compound class.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

AutoNom 2000 (Automatic Nomenclature) for ISIS/Draw was employed to generate IUPAC chemical names.

Any open valency appearing on a carbon, oxygen, sulfur or nitrogen atom in the structures herein indicates the presence of a hydrogen, unless indicated otherwise.

The term "moiety" refers to an atom or group of chemically bonded atoms that is attached to another atom or molecule by one or more chemical bonds thereby forming part of a molecule. For example, the variables $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term, "structurally related substances" denotes substances that share a common or core structure of the substance that has biological activity, such as a common pharmacophore or olfactophore. Such structurally related substances can differ from each other, however, in their substituent groups.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "halo", "halogen", and "halide" are used interchangeably herein and denote fluoro, chloro, bromo, or iodo. Particular examples of halo are fluoro and chloro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl are methyl, ethyl, isopropyl, n-butyl, sec-butyl and tert-butyl, most particularly methyl and ethyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy is methoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples of haloalkyl is trifluoromethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular cycloalkyl is cyclopropyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl are pyrrolidinyl, piperidinyl, piperazinyl, morpholinyl, 2-oxa-5-aza-bicyclo[2.2.1]heptyl and dihydropyranyl. Particular examples of saturated heterocycloalkyl are pyrrolidinyl, piperidinyl, piperazinyl, morpholinyl and 2-oxa-5-aza-bicyclo[2.2.1]heptyl. Particular examples of partly unsaturated heterocycloalkyl are dihydropyranyl and dihydroindolyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl, most particularly phenyl. Particular aryl substituted by aryl is biphenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular examples of heteroaryl are imidazolyl, pyrazolyl, pyrrolyl, isoxazolyl, pyridinyl, pyrazinyl, pyridazinyl, pyrimidinyl, indolyl and quinolyl. Most particular examples of heteroaryl are pyridinyl and indolyl.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups.

The term "carboxy-protecting group" denotes groups intended to protect a carboxy group and includes ester groups and heterocycloalkyl groups. Examples of such ester groups include substituted arylalkyl esters, including esters with substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, esters with alkyl or substituted alkyl such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, and 1-(trimethylsilylmethyl)prop-1-en-3-yl. Another example of carboxy-protecting groups are heterocycloalkyl groups such as 1,3-oxazolinyl. Further examples of these groups are found in T. W. Greene and P. G. M. Wuts, "Protective Groups in Organic Synthesis", 2nd ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy group" denotes a carboxy group substituted by a carboxy-protecting group.

The term "hydroxy-protecting group" denotes groups intended to protect a hydroxy group and include ester- and ether-forming groups, in particular tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy group" refers to a hydroxy group substituted by a hydroxy-protecting group.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

The term "amino acid" as used herein denotes an organic molecule possessing an amino moiety located at a-position to a carboxylic group. Examples of amino acids include: arginine, glycine, ornithine, lysine, histidine, glutamic acid, asparagic acid, isoleucine, leucine, alanine, phenylalanine, tyrosine, tryptophane, methionine, serine, proline. The amino acid employed is optionally in each case the L-form.

In detail, the present invention relates to a compound of formula (A)

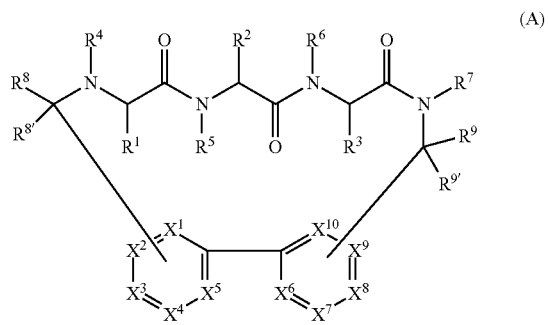

(A)

wherein:

$X^1$ is C—$R^{11}$ or N, $X^2$ is C—$R^{12}$ or N, $X^3$ is C—$R^{13}$ or N, $X^4$ is C—$R^{14}$ or N, $X^5$ is C—$R^{15}$ or N, with the proviso that not more than three of $X^1$, $X^2$, $X^3$, $X^4$ and $X^5$ are N;

$X^6$ is C—$R^{16}$ or N, $X^7$ is C—$R^{17}$ or N, $X^8$ is C—$R^{18}$ or N, $X^9$ is C—$R^{19}$ or N, $X^{10}$ is C—$R^{20}$ or N, with the proviso that not more than three of $X^6$, $X^7$, $X^8$, $X^9$ and $X^{10}$ are N;

$R^{11}$, $R^{12}$, $R^{13}$, $R^{14}$, $R^{15}$, $R^{16}$, $R^{17}$, $R^{18}$, $R^{19}$ and $R^{20}$ are each individually selected from a bond, hydrogen, halogen, $C_{1-7}$-alkyl, $C_{1-7}$-haloalkyl and $C_{1-7}$-alkoxy;

$R^1$ and $R^2$ are each independently selected from hydrogen, —$C_{1-7}$-alkyl, hydroxy-$C_{1-7}$-alkyl, —$(CH_2)_m$—$NR^{20}R^{21}$, —$(CH_2)_m$—C(O)$NR^{20}R^{21}$, —$(CH_2)_m$—$CF_2$—$(CH_2)_m$—$NR^{20}R^{21}$, —$(CH_2)_m$—NH—C(O)—$(CH_2)_m$—$NR^{20}R^{21}$ or —$(CH_2)_m$—O—$(CH_2)_o$—$NR^{20}R^{21}$, —$(CH_2)_m$—NH—C(NH)—$NR^{20}R^{21}$, —$(CH_2)_m$—NH—C(O)—$OR^{21}$, —$(CH_2)_o$ —$C_{3-7}$-cycloalkyl, —$(CH_2)_o$-heterocycloalkyl, —$(CH_2)_o$-heteroaryl, —$(CH_2)_o$-aryl, wherein cycloalkyl, heterocycloalkyl, heteroaryl and aryl are optionally substituted by halo, cyano, $C_{1-7}$-alkyl, $C_{1-7}$-haloalkyl, $C_{1-7}$-hydroxyalkyl, $C_{1-7}$-alkoxy or aryl;

$R^3$ is —$(CH_2)_m$-heteroaryl or —$(CH_2)_m$-heterocycloalkyl, wherein heteroaryl is optionally substituted with one or more halo, cyano, $C_{1-7}$-alkyl, $C_{1-7}$-haloalkyl, $C_{3-7}$-cycloalkyl or $C_{1-7}$-alkoxy;

$R^4$, $R^5$, $R^6$ and $R^7$ are each individually selected from hydrogen, $C_{1-7}$-alkyl, $C_{1-7}$-haloalkyl, hydroxy-$C_{1-7}$-alkyl, alkoxy-$C_{1-7}$-alkyl, —$(CH_2)_o$—$NR^{20}R^{21}$, —$(CH_2)_o$—$C_{3-7}$-cycloalkyl, —$(CH_2)_o$-heterocycloalkyl, wherein cycloalkyl and heterocycloalkyl are optionally substituted by halo, cyano, $C_{1-7}$-alkyl, $C_{1-7}$-haloalkyl, $C_{1-7}$-hydroxyalkyl, $C_{1-7}$-alkoxy or aryl;

$R^8$, $R^{8'}$, $R^9$ and $R^{9'}$ are each individually selected from hydrogen and $C_{1-3}$-alkyl;

m is 1, 2, 3, 4, 5 or 6;

n is 2, 3, 4, 5 or 6;

o is 0, 1, 2, 3, 4, 5 or 6;

or a pharmaceutically acceptable salt thereof.

Particular embodiments of the present invention are compounds of formula (I) or a pharmaceutically acceptable salt thereof. Further, it is to be understood that every embodiment relating to a specific $X^1$ to $X^2$, $R^1$ to $R^{20}$, m, n, or o disclosed herein may be combined with any other embodiment relating to another $X^1$ to $X^2$, $R^1$ to $R^{20}$, m, n, o, p or q as disclosed herein.

A particular embodiment of the present invention relates to a compound of formula (Ia)

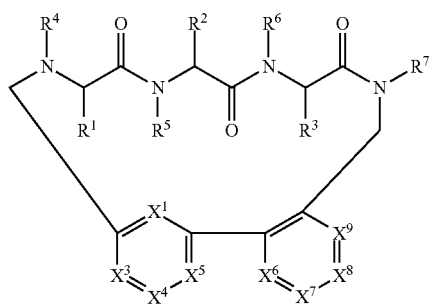

(Ia)

wherein $X^1$ is C—$R^{11}$ or N, $X^3$ is C—$R^{13}$ or N, $X^4$ is C—$R^{14}$ or N, $X^5$ is C—$R^{15}$ or N, with the proviso that not more than one of $X^1$, $X^3$, $X^4$ and $X^5$ is N;

$X^6$ is C—$R^{16}$ or N, $X^7$ is C—$R^{17}$ or N, $X^8$ is C—$R^{18}$ or N, $X^9$ is C—$R^{19}$ or N, with the proviso that not more than one of $X^5$, $X^6$, $X^7$, $X^8$ and $X^9$ is N;

$R^{11}$, $R^{13}$, $R^{14}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy;

$R^1$ is $C_{1-7}$-alkyl, —$(CH_2)_m$—$NH_2$ or —$(CH_2)_n$—O—$(CH_2)_p$—$NH_2$;

$R^2$ is —$C_{1-7}$-alkyl, —$(CH_2)_m$—$NH_2$ or —$(CH_2)_n$—O—$(CH_2)_q$—$NH_2$;

$R^3$ is —$(CH_2)_m$-heteroaryl optionally substituted with one or more halo, $C_{1-7}$-alkyl, $C_{1-7}$-haloalkyl or $C_{1-7}$-alkoxy;

$R^4$, $R^5$, $R^6$ and $R^7$ are each individually selected from hydrogen and $C_{1-3}$-alkyl;

m is 1, 2, 3, 4, 5 or 6;

n is 2, 3, 4, 5 or 6;

o is 0, 1, 2, 3, 4, 5 or 6;

or a pharmaceutically acceptable salt thereof.

Another particular embodiment of the present invention relates to a compound of formula (Ia')

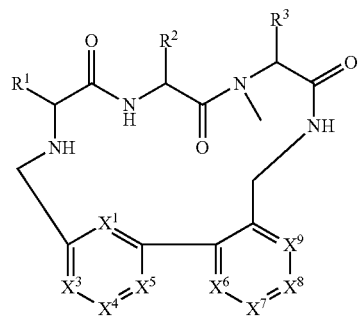

(Ia')

wherein:

$X^1$ is C—$R^{11}$ or N, $X^3$ is C—$R^{13}$ or N, $X^4$ is C—$R^{14}$ or N, $X^5$ is C—$R^{15}$ or N, with the proviso that not more than one of $X^1$, $X^3$, $X^4$ and $X^5$ is N;

$X^6$ is C—$R^{16}$ or N, $X^7$ is C—$R^{17}$ or N, $X^8$ is C—$R^{18}$ or N, $X^9$ is C—$R^{19}$ or N, with the proviso that not more than one of $X^5$, $X^6$, $X^7$, $X^8$ and $X^9$ is N;

$R^{11}$, $R^{13}$, $R^{14}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy;

$R^1$ is —$(CH_2)_m$—$NH_2$;

$R^2$ is —$(CH_2)_m$—$NH_2$;

$R^3$ is —$(CH_2)_m$-heteroaryl optionally substituted with one or more halo, $C_{1-7}$-alkyl, $C_{1-7}$-haloalkyl or $C_{1-7}$-alkoxy;

m is 1, 2 or 3;

n is 1, 2, 3, or 4;

o is 1, 2, 3, or 4;

or a pharmaceutically acceptable salt thereof.

Another particular embodiment of the present invention relates to a compound of formula (Ia")

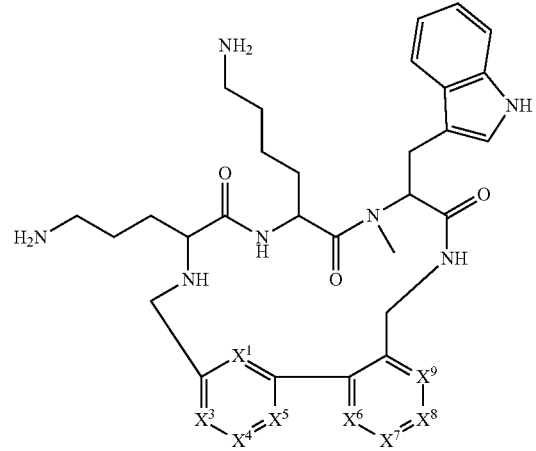

(Ia")

wherein:

$X^1$ is C—$R^{11}$ or N, $X^3$ is C—$R^{13}$ or N, $X^4$ is C—$R^{14}$ or N,
$X^5$ is C—$R^{15}$ or N, with the proviso that not more than one of $X^1$, $X^3$, $X^4$ and $X^5$ is N;
$X^6$ is C—$R^{16}$ or N,
$X^7$ is C—$R^{17}$ or N,
$X^8$ is C—$R^{18}$ or N,
$X^9$ is C—$R^{19}$ or N, with the proviso that not more than one of $X^5$, $X^6$, $X^7$, $X^8$ and $X^9$ is N;
$R^{11}$, $R^{13}$, $R^{14}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy;
or a pharmaceutically acceptable salt thereof.

Another particular embodiment of the present invention relates to a compound of formula (Ia''')

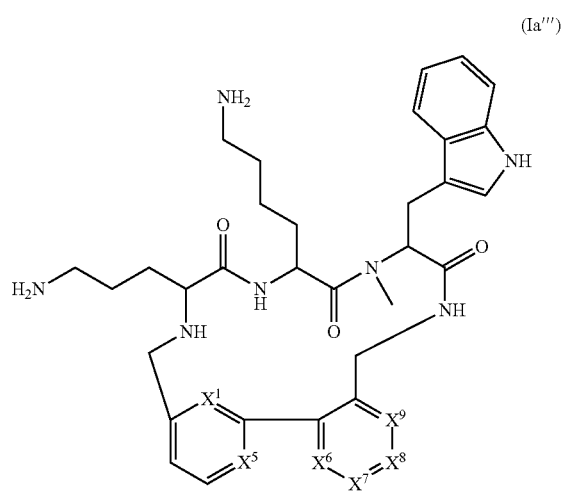

(Ia''')

wherein:
$X^1$ is C—$R^{11}$ or N,
$X^5$ is C—$R^{15}$ or N, with the proviso that not more than one of $X^1$ and $X^5$ is N;
$X^6$ is C—$R^{16}$ or N,
$X^7$ is C—$R^{17}$ or N,
$X^8$ is C—$R^{18}$ or N,
$X^9$ is C—$R^{19}$ or N, with the proviso that not more than one of $X^5$, $X^6$, $X^7$, $X^8$ and $X^9$ is N;
$R^{11}$, $R^{13}$, $R^{14}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy;
or a pharmaceutically acceptable salt thereof.

In a particular embodiment of the present invention $X^1$ is CH, $X^5$ is CH, $X^6$ is C—$R^{16}$, $X^7$ is C—$R^{17}$, $X^8$ is C—$R^{18}$, $X^9$ is C—$R^{19}$;
$R^{16}$, $R^{17}$, $R^{18}$ and $R^{19}$ are each individually selected from hydrogen, halogen, $C_{1-3}$-alkyl, $C_{1-3}$-haloalkyl and $C_{1-3}$-alkoxy;
or a pharmaceutically acceptable salt thereof.

Particular compounds of formula (I) of the present invention are those selected from the group consisting of:
(11S,14S,17S)-14-(4-Amino-butyl)-17-(3-amino-propyl)-11-(1H-indol-3-ylmethyl)-12-methyl-9,12,15,18-tetraaza-tricyclo[18.3.1.0*2,7*]tetracosa-1(24),2(7),3,5,20,22-hexaene-10,13,16-trione;
(11S,14S,17S)-14-(4-Amino-butyl)-17-(3-amino-propyl)-11-(1H-indol-3-ylmethyl)-12-methyl-3-trifluoromethyl-9,12,15,18-tetraaza-tricyclo[18.3.1.0*2,7*]tetracosa-1(24),2(7),3,5,20,22-hexaene-10,13,16-trione;
(11S,14S,17S)-14-(4-Amino-butyl)-17-(3-amino-propyl)-11-(1H-indol-3-ylmethyl)-12-methyl-5-trifluoromethyl-9,12,15,18-tetraaza-tricyclo[18.3.1.0*2,7*]tetracosa-1(24),2(7),3,5,20,22-hexaene-10,13,16-trione;
(11S,14S,17S)-14-(4-Amino-butyl)-17-(3-amino-propyl)-11-(1H-indol-3-ylmethyl)-3,12-dimethyl-9,12,15,18-tetraaza-tricyclo[18.3.1.0*2,7*]tetracosa-1 (23),2(7),3,5,20 (24),21-hexaene-10,13,16-trione;
(11S,14S,17S)-14-(4-Amino-butyl)-17-(3-amino-propyl)-5-chloro-11-(1H-indol-3-ylmethyl)-12-methyl-9,12,15,18-tetraaza-tricyclo[18.3.1.0*2,7]tetracosa-1(23),2(7),3,5,20 (24),21-hexaene-10,13,16-trione;
(11S,14S,17S)-14-(4-Amino-butyl)-17-(3-amino-propyl)-6-chloro-11-(1H-indol-3-ylmethyl)-12-methyl-9,12,15,18-tetraaza-tricyclo[18.3.1.0*2,7*]tetracosa-1(23),2(7),3,5,20(24),21-hexaene-10,13,16-trione;
(11S,14S,17S)-14-(4-Amino-butyl)-17-(3-amino-propyl)-11-(1H-indol-3-ylmethyl)-5,12-dimethyl-9,12,15,18-tetraaza-tricyclo[18.3.1.0*2,7*]tetracosa-1(23),2(7),3,5,20 (24),21-hexaene-10,13,16-trione;
(11S,14S,17S)-14-(4-Amino-butyl)-17-(3-amino-propyl)-11-(1H-indol-3-ylmethyl)-12-methyl-4-trifluoromethyl-9,12,15,18-tetraaza-tricyclo[18.3.1.0*2,7]tetracosa-1 (24),2(7),3,5,20,22-hexaene-10,13,16-trione;
(11S,14S,17S)-14-(4-Amino-butyl)-17-(3-amino-propyl)-11-(1H-indol-3-ylmethyl)-5-methoxy-12-methyl-9,12,15,18-tetraaza-tricyclo[18.3.1.0*2,7]tetracosa-1(23),2(7),3,5,20(24),21-hexaene-10,13,16-trione;
(11S,14S,17S)-14-(4-Amino-butyl)-17-(3-amino-propyl)-24-fluoro-11-(1H-indol-3-ylmethyl)-12-methyl-9,12,15,18-tetraaza-tricyclo[18.3.1.0*2,7*]tetracosa-1(23),2(7),3,5,20(24),21-hexaene-10,13,16-trione; and
(11S,14S,17S)-14-(4-Amino-butyl)-17-(3-amino-propyl)-5-chloro-11-(1H-indol-3-ylmethyl)-12-methyl-9,12,15,18,23-pentaaza-tricyclo[18.3.1.0*2,7*]tetracosa-1(23),2(7),3,5,20(24),21-hexaene-10,13,16-trione;
and pharmaceutically acceptable salts thereof.

More particular compounds of formula (I) of the present invention are those selected from the group consisting of:
(11S,14S,17S)-14-(4-Amino-butyl)-17-(3-amino-propyl)-11-(1H-indol-3-ylmethyl)-12-methyl-3-trifluoromethyl-9,12,15,18-tetraaza-tricyclo[18.3.1.0*2,7*]tetracosa-1 (24),2(7),3,5,20,22-hexaene-10,13,16-trione;
(11S,14S,17S)-14-(4-Amino-butyl)-17-(3-amino-propyl)-11-(1H-indol-3-ylmethyl)-12-methyl-5-trifluoromethyl-9,12,15,18-tetraaza-tricyclo[18.3.1.0*2,7*]tetracosa-1 (24),2(7),3,5,20,22-hexaene-10,13,16-trione;
(11S,14S,17S)-14-(4-Amino-butyl)-17-(3-amino-propyl)-5-chloro-11-(1H-indol-3-ylmethyl)-12-methyl-9,12,15,18-tetraaza-tricyclo[18.3.1.0*2,7]tetracosa-1(23),2(7),3,5,20 (24),21-hexaene-10,13,16-trione;
(11S,14S,17S)-14-(4-Amino-butyl)-17-(3-amino-propyl)-11-(1H-indol-3-ylmethyl)-5,12-dimethyl-9,12,15,18-tetraaza-tricyclo[18.3.1.0*2,7*]tetracosa-1(23),2(7),3,5,20 (24),21-hexaene-10,13,16-trione;
(11S,14S,17S)-14-(4-Amino-butyl)-17-(3-amino-propyl)-11-(1H-indol-3-ylmethyl)-12-methyl-4-trifluoromethyl-9,12,15,18-tetraaza-tricyclo[18.3.1.0*2,7*]tetracosa-1 (24),2(7),3,5,20,22-hexaene-10,13,16-trione;
(11S,14S,17S)-14-(4-Amino-butyl)-17-(3-amino-propyl)-11-(1H-indol-3-ylmethyl)-5-methoxy-12-methyl-9,12,15,18-tetraaza-tricyclo[18.3.1.0*2,7]tetracosa-1(23),2(7),3,5,20(24),21-hexaene-10,13,16-trione;
and pharmaceutically acceptable salts thereof Manufacturing Processes Compounds of formula (Ia) or (Ib) and pharmaceutically acceptable salts thereof as defined above can be prepared following standard methods known in the art.

1. General synthesis of the tether

The tether intermediate of formula (III) can be prepared following standard methods known in the art, particularly according to methods as described in the examples (e.g. PG=Fmoc).

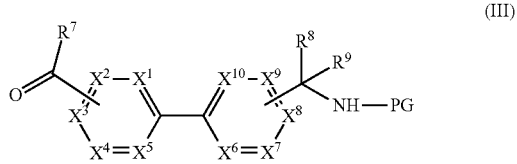

(III)

2. General synthesis of the tripeptide

The tripeptide of formula (IV) can be prepared following standard methods known in the art.

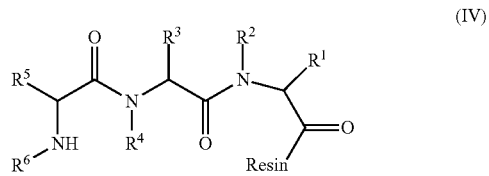

(IV)

The tripeptide sequence can for example be synthesized via state-of-the-art solid-phase peptide synthesis (SPPS) protocols (e.g. Fmoc-chemistry) as follows:

a) A resin (e.g. 2-Cl-Trityl resin) as solid support is loaded with the first N-protected amino acid and Hüinig's base (N,N-Diisopropylethylamine or DIPEA) followed by cleavage of the protecting group.
b) A second N-protected amino acid is coupled with a coupling reagent and Hüinig's base followed by cleavage of the protecting group (e.g. Fmoc).
c) A third N-protected amino acid is coupled with a coupling reagent and Hüinig's base followed by cleavage of the protecting group.

In a particular embodiment, the solid support is a 2-Chlortritylchloride resin.

In a particular embodiment, the N-protected amino acids are protected with 9-fluorenylmethyloxycarbonyl (Fmoc).

In a particular embodiment, the resin is loaded in step a) with 0.1-1.0 eq of the first amino acid and excess Hüinig's base in dichloromethane (DCM).

In a particular embodiment, the resin is thoroughly washed after the coupling reaction in step a) with dimethylformamide (DMF) and dichloromethane (DCM).

In a particular embodiment, the Fmoc protecting group is cleaved off in step a) with a mixture of 50% Piperidine in DCM/DMF (1:1).

In a particular embodiment, the resin is thoroughly washed after the deprotection in step a) with DMF, DCM and Methanol (MeOH) followed by drying under vacuum and weighing.

In a particular embodiment, the coupling reagent in step b) is Mukaiyama's reagent (2-chloro-1-methylpyridinium iodide).

In a particular embodiment, the second amino acid in step b) is coupled with 4 eq of Mukaiyama's reagent as coupling reagent and 6 eq of Hüinig's base in DMF/DCM (1:1).

In a particular embodiment, the resin is thoroughly washed after the coupling reaction in step b) with dimethylformamide (DMF) and dichloromethane (DCM).

In a particular embodiment, the Fmoc protecting group is cleaved off in step b) with a mixture of 50% Piperidine in DCM/DMF (1:1).

In a particular embodiment, the resin is thoroughly washed after the deprotection in step b) with DMF and DCM followed by drying under vacuum and weighing.

In a particular embodiment, the coupling reagent in step c) is HATU (1-[bis(dimethyl-amino)methylene]-1H-1,2,3-triazolo[4,5-b]pyridinium 3-oxid hexafluorophosphate).

In a particular embodiment, the third amino acid in step c) is coupled with 4 eq of HATU as coupling reagent and 6 eq of Hüinig's base in DMF/DCM (1:1).

In a particular embodiment, the resin is thoroughly washed after the coupling reaction in step c) with dimethylformamide (DMF) and dichloromethane (DCM).

In a particular embodiment, the Fmoc protecting group is cleaved off in step c) with a mixture of 20% Piperidine in DMF.

In a particular embodiment, the resin is thoroughly washed after the deprotection in step c) with DMF and DCM followed by drying under vacuum and weighing.

3. General synthesis for the coupling of the tripeptide to the tether

The compound of formula (Ia) or (Ib) can be obtained starting from the compounds of formula (III) and of formula (IV) according to Scheme 1.

Scheme 1.

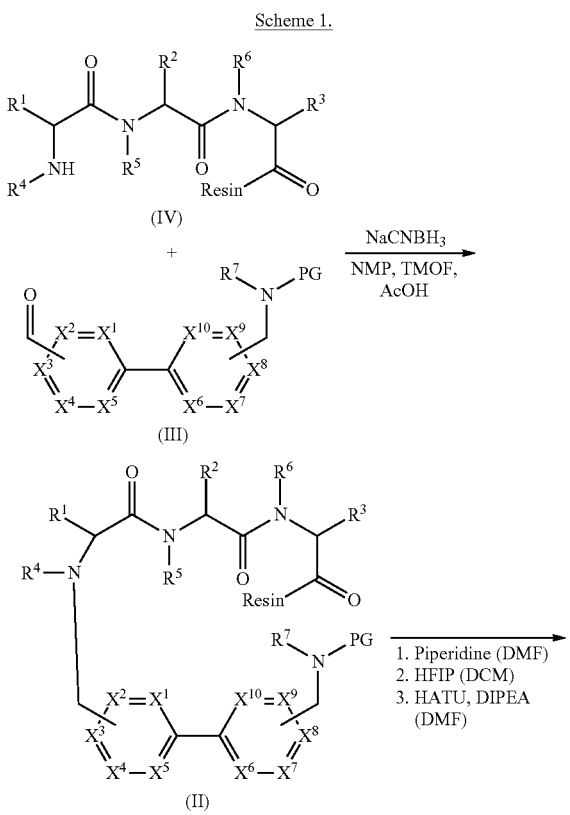

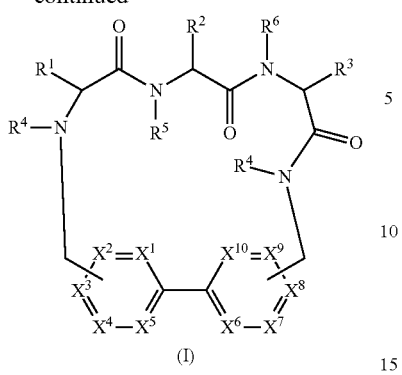

(I)

The tether aldehyde or ketone of formula (III) is dissolved in a mixture of N-methyl-2-pyrrolidone (NMP), trimethyl orthoformate (TMOF) and acetic acid (AcOH) and the resin comprising the tripeptide of formula (IV) is added to the solution. After agitation of the mixture, sodium cyanoborohydride (NaCNBH$_3$) is added to provide a compound of formula (II).

After the Borch reaction, the protecting group (PG) on the tether is cleaved off, e.g. with a mixture of 20% Piperidine in DMF. The resin on the tripeptide can be cleaved e.g. by addition of 20% hexafluoroisopropanol (HFIP) in DCM and filtered off. The compound of formula (I) is finally obtained through cyclisation of the cleaved compound of formula (II) using HATU and Hünig's base followed by global deprotection of remaining protected amine groups.

A particular embodiment of the invention relates to a process for the manufacture of a compound of formula (I) comprising the steps of:

a) reacting a compound of formula (III) with a compound of formula (IV) using sodium cyanoborohydride (NaCNBH$_3$) to provide a compound of formula (II);

Scheme 1.

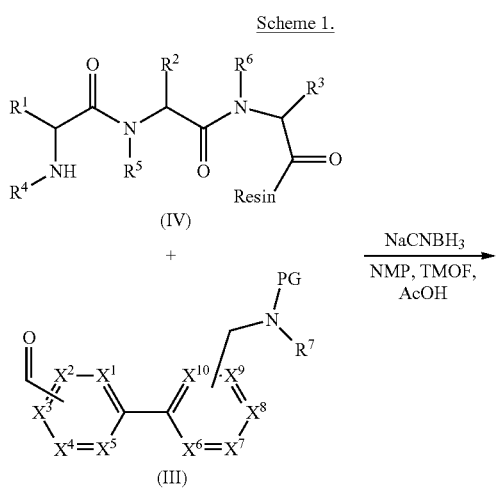

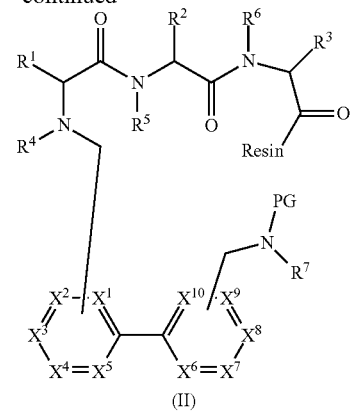

(II)

b) cleaving off the protecting group (PG) and the resin from the compound of formula (II);

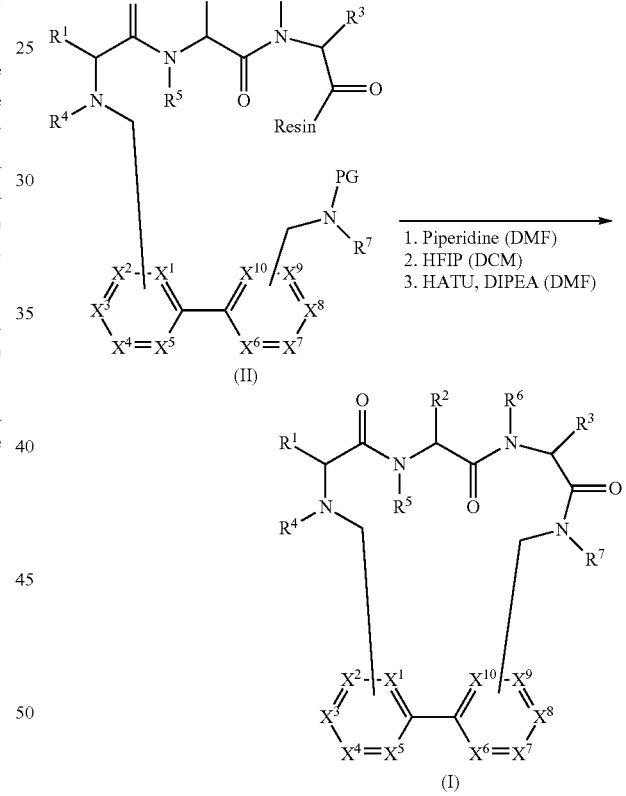

c) followed by cyclisation of the cleaved compound of formula (II) using HATU and Hünig's base.

In particular embodiment, the tripeptide of formula (IV) is washed with DCM prior to adding it to the tether aldehyde or ketone of formula (III).

In a particular embodiment, the solvent of the tether aldehyde of formula (III) consists of a mixture of N-methyl-2-pyrrolidone (NMP), trimethyl orthoformate (TMOF) and acetic acid (AcOH).

In a particular embodiment, the reaction mixture is washed after the Borch reaction with DMF, DCM, MeOH/DCM and/or DMF.

In a particular embodiment, the cyclization of the deprotected and cleaved compound of formula (II) takes place using HATU and DIPEA in DMF.

In a particular embodiment, the global BOC-deprotection is achieved by treatment with TFA in a solvent, particularly DCM, at RT.

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

Uses

As described above, the compounds of formula (Ia) or (Ib) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii*.

The compounds of formula (Ia) or (Ib) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii*.

The compounds of formula (Ia) or (Ib) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii*.

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to pharmaceutical compositions comprising compounds of formula (Ia) or (Ib) as defined above or their pharmaceutically acceptable salts as defined above and one or more pharmaceutically acceptable excipients.

A particular embodiment of the present invention relates to pharmaceutical compositions comprising compounds of formula (Ia) or (Ib) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to compounds of formula (Ia) or (Ib) or their pharmaceutically acceptable salts as defined above for use as therapeutically active substances, especially for use as therapeutically active substances for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to compounds of formula (Ia) or (Ib) or their pharmaceutically acceptable salts as defined above for the use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering compounds of formula (Ia) or (Ib) or their pharmaceutically acceptable salts as defined above to a subject.

A particular embodiment of the present invention relates to the use of compounds of formula (Ia) or (Ib) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to the use of compounds of formula (Ia) or (Ib) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*. Such medicaments comprise compounds of formula (Ia) or (Ib) or their pharmaceutically acceptable salts as defined above.

EXAMPLES

The invention will be more fully understood by reference to the following examples. They should however not be construed as limiting the scope of the invention.

Abbreviations Used
Agp: 2-amino-3-guanidino-propionic acid
Boc: tert. Butyloxycarbonyl
DCM: Dichlormethane
DIPEA: N,N-Diisopropylamine
DMF: N,N-Dimethylformamide
EA: Ethyl acetate
EtOAc: Ethyl acetate
EtOH: Ethanol
Fmoc: 9-Fluorenylmethoxycarbonyl
Fmoc-OSu: N-(9-Fluorenylmethoxycarbonyloxy)succinimide
HATU: 0-(7-Azabenzotriazol-1-yl)-N,N,N',N'-tetramethyluronium-hexafluorophosphate
HFIP: Hexafluoroisopropanol
HOBt: Hydroxy-benzotriazole
LAH: Lithium aluminium hydride
Lys: Lysine MeCN: Acetonitrile
Mukaiyama's reagent: 2-Chloro-1-methyl-pyridinium iodide
MTBD: 7-Methyl-1,5,7-triazabicyclo[4.4.0]dec-5-ene
NMP: N-Methylprolidone
Orn: Ornithine
Pd2(dba)$_3$: Tris(dibenzylideneacetone)dipalladium(0)
THF: tetrahydrofurane
TLC: Thin layer chromatography
TMOF: Trimethyl-orthoformiate
Trp: Tryptophane
p-TSA: p-Toluenesulfonic acid or tosylic acid
HMPA: Hexamethylphosphoramide Intermediate 1

9H-fluoren-9-ylmethyl N-[[2-(3-formylphenyl)phenyl]methyl]carbamate

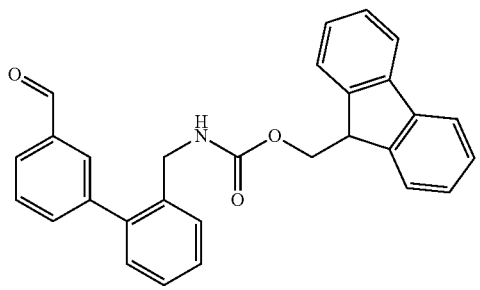 [SMILES: O=Cc1cccc(-c2ccccc2CNC(=O)OCC2c3ccccc3-c3ccccc32)c1]

To a solution of (2-bromophenyl)methanamine (1 g, 5.37 mmol, Eq: 1) in MeOH (30 mL) was added pyridine (1.28 g, 1.3 ml, 16.1 mmol, Eq: 3) and 9-fluorenylmethyl-N-succinimidyl carbonate (1.81 g, 5.37 mmol, Eq: 1). A very thick precipitation occurred. MeOH (40 mL) was added. The suspension was stirred for 2 hours at room temperature. The reaction mixture was poured on 150 mL 10% aqueous NaHCO3 solution and 150 mL EtOAc and the layers were separated. The aqueous layer was extracted a second time with 100 mL EtOAc. The organic layers were washed with 100 mL brine, dried over MgSO4, filtered and concentrated under vacuum. The yellow solid was dissolved in 100 mL MeOH at reflux. The yellow solution was allowed to cool to room temperature and then stirred for 30 minutes at 0° C. The white solid was filtrated and dried under vacuum to yield 9H-fluoren-9-ylmethyl N-[(2-bromophenyl)methyl] carbamate (1.65 g, 75.2%). MS (ESI): m/z=408.058 [M+H]+.

To a solution of (3-(methoxycarbonyl)phenyl)boronic acid (245 mg, 1.36 mmol, Eq: 1.5) in THF (6 mL) was added 9H-fluoren-9-ylmethyl N-[(2-bromophenyl)methyl]carbamate (370 mg, 906 µmol, Eq: 1) and potassium fluoride (105 mg, 1.81 mmol, Eq: 2). The reaction mixture was degassed under a slight argon flush in an ultrasonic bath for 15 minutes. palladium(II)acetate (4.07 mg, 18.1 µmol, Eq: 0.02) and (2-biphenyl)di-tert-butylphosphine (10.8 mg, 36.2 µmol, Eq: 0.04) was added. The reaction mixture was stirred for 18 hours at 35° C. The reaction mixture was poured on 30 mL 10% aqueous citric acid and 30 mL EtOAc and the layers were separated. The aqueous layer was extracted a second time with 30 mL EtOAc. The organic layers were washed with 30 mL water and 30 mL brine, dried over MgSO4, filtered and concentrated under vacuum. The residue was purified by silica gel to yield methyl 3-[2-[(9H- fluoren-9-ylmethoxycarbonylamino)methyl]phenyl]benzoate as a white solid (135 mg, 32%). MS (ER): m/z=464.2 [M+H]+.

To a solution of methyl 3-[2-[(9H-fluoren-9-ylmethoxycarbonylamino)methyl]phenyl]benzoate (128 mg, 276 µmol, Eq: 1) in toluene (4 mL) was added at −75° C. and under argon dropwise diisobutylaluminiumhydide solution 25 wt. % in toluene (267 mg, 315 µL, 469 nmol, Eq: 1.7). The reaction mixture was stirred for 2 hours at −0° C. TLC showed still about 50% starting material. Again diisobutylaluminiumhydide solution 25 wt. % in toluene (267 mg, 315 µL, 469 nmol, Eq: 1.7) was added. The reaction mixture was stirred for further 30 minutes at room temperature. TLC showed complete conversion. The reaction mixture was poured on 30 mL saturated aqueous potassium sodium tartrate solution and 30 mL EtOAc. The layers were filtered over a pad of dicalite and the layers were separated. The aqueous layer was extracted a second time with 30 mL EtOAc. The organic layers were washed with 30 mL brine, dried over MgSO4, filtered and concentrated under vacuum. The residue was purified by silica gel chromatography on a 20 g column using an MPLC system (CombiFlash Companion, Isco Inc.) eluting with a gradient of n-heptane:ethyl acetate (100:0 to 30:70) to yield 9H-fluoren-9-ylmethyl N-[[2-[3-(hydroxymethyl)phenyl]phenyl]methyl]carbamate as a white foam (57 mg, 47.4%). MS (ER): m/z=436.191 [M+H]+.

To a solution of 9H-fluoren-9-ylmethyl N-[[2-[3-(hydroxymethyl)phenyl]phenyl]methyl]carbamate (55 mg, 126 nmol, Eq: 1) in DCM (1 mL) and THF (1 mL) was added manganese(IV) oxide activated (220 mg, 2.53 mmol, Eq: 20). The reaction mixture was stirred for 3 hours at room temperature. The reaction mixture was filtered over a pad of dicalite and washed with EtOAc. The filtrate was concentrated under vacuum to yield 9H-fluoren-9-ylmethyl N-[[2-(3-formylphenyl)phenyl]methyl]carbamate (57 mg, 47%). LCMS: m/z=434.2 [M+H+]+

1H NMR (600 MHz, DMSO-d6) δ ppm 4.13 (d, J=5.8 Hz, 2H) 4.20 (s, 1H) 4.30 (d, J=7.0 Hz, 2H) 7.26 (br d, J=7.0 Hz, 1H) 7.30-7.35 (m, 1H) 7.32-7.44 (m, 6H) 7.40-7.44 (m, 2H) 7.65 (s, 2H) 7.68 (0,=8.1 Hz, 2H) 7.70-7.74 (m, 1H) 7.81 (s, 1H) 7.86-7.93 (m, 2H) 7.87-7.89 (m, 1H) 10.05 (s, 1H)

Intermediate 2

9H-fluoren-9-ylmethyl N-[[2-(3-formylphenyl)-3-(trifluoromethyl)phenyl]methyl]carbamate

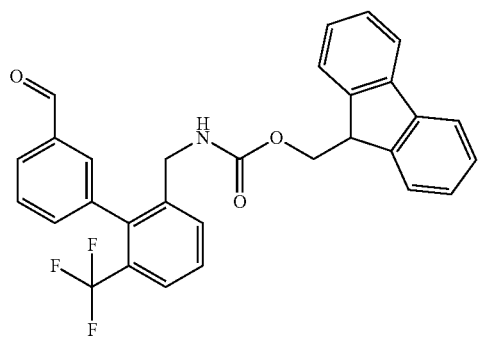 [SMILES: O=Cc1cccc(-c2c(CNC(=O)OCC3c4ccccc4-c4ccccc43)cccc2C(F)(F)F)c1]

To a solution of (2-bromo-3-(trifluoromethyl)phenyl) methanamine hydrochloride (2 g, 6.88 mmol, Eq: 1) in MeOH (60 ml) was added pyridine (2.18 g, 2.22 ml, 27.5 mmol, Eq: 4) and 9-fluorenylmethyl-N-succinimidyl carbonate (2.32 g, 6.88 mmol, Eq: 1). A very thick precipitation occurred. MeOH (80 ml) was added. The suspension was stirred over night at room temperature. The reaction mixture was poured on 230 mL 10% aqueous NaHCO3 solution and 230 mL EtOAc and the layers were separated. The aqueous layer was extracted a second time with 230 mL EtOAc. The organic layers were washed with 230 mL water and 230 mL brine, dried over MgSO4, filtered and concentrated under vacuum. The yellow solid was dissolved in 180 mL MeOH at reflux. The yellow solution was allowed to cool to room temperature and then stirred for 30 minutes at 0° C. The white solid was filtrated and dried under vacuum to yield 9H-fluoren-9-ylmethyl N-[[2-bromo-3-(trifluoromethyl) phenyl]methyl]carbamate (1.74 g, 53.2%). MS (ESI): m/z=478.1 [M+H]+.

To a solution of (3-(methoxycarbonyl)phenyl)boronic acid (227 mg, 1.26 mmol, Eq: 1.5) in THF (8 mL) was added 9H-fluoren-9-ylmethyl N-[[2-bromo-3-(trifluoromethyl) phenyl]methyl]carbamate (400 mg, 840 µmol, Eq: 1) and potassium fluoride (146 mg, 2.52 mmol, Eq: 3). The reaction mixture was degassed under a slight argon flush in an ultrasonic bath for 15 minutes. palladium(II)acetate (3.77 mg, 16.8 µmol, Eq: 0.02) and (2-biphenyl)di-tert-butylphosphine (10 mg, 33.6 µmol, Eq: 0.04) was added. The reaction mixture was stirred for 18 hours at 40° C. The reaction mixture was poured on 30 mL 10% aqueous citric acid solution and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield of methyl 3-[2-[(9H-fluoren-9-ylmethoxycarbonylamino)methyl]-6-(trifluoromethyl)phenyl]benzoate as white foam (142 mg, 31.8%). MS (ESI): m/z=532.174 [M+H]+.

To a solution of methyl 3-[2-[(9H-fluoren-9-ylmethoxycarbonylamino)methyl]-6-(trifluoromethyl)phenyl]benzoate (140 mg, 263 µmol, Eq: 1) in toluene (4 mL) was added at −75° C. and under argon dropwise diisobutylaluminiumhydide solution 25 wt. % in toluene (255 mg, 301 µL, 448 µmol, Eq: 1.7). The reaction mixture was stirred for 2 hours at −0° C. TLC showed still about 50% starting material. Again diisobutylaluminiumhydide solution 25 wt. % in toluene (255 mg, 301 µL, 448 µmol, Eq: 1.7) was added. The reaction mixture was stirred for further 30 minutes at 0° C. TLC showed complete conversion. The reaction mixture was poured on 30 mL saturated aqueous potassium sodium tartrate solution and 30 mL EtOAc. The layers were filtered over a pad of dicalite and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield (9H-fluoren-9-yl)methyl ((3'-(hydroxymethyl)-6-(trifluoromethyl)-[1,1'-biphenyl]-2-yl)methyl)carbamate as a white foam (54 mg, 40.7%). MS (ER): m/z=504.178 [M+H]+.

To a solution of (9H-fluoren-9-yl)methyl 43'-(hydroxymethyl)-6-(trifluoromethyl)-[1,1'-biphenyl]-2-yl)methyl)carbamate (48 mg, 95.3 µmol, Eq: 1) in DCM (1 mL) and THF (1 mL) was added manganese(IV) oxide activated (166 mg, 1.91 mmol, Eq: 20). The reaction mixture was stirred for 3 hours at room temperature. The reaction mixture was filtered over a pad of dicalite and washed with EtOAc. The filtrate was concentrated under vacuum. 9H-fluoren-9-ylmethyl N-[[2-(3-formylphenyl)-3-(trifluoromethyl)phenyl]methyl]

carbamate was obtained as a light yellow foam (40 mg, 83.7%). MS (ESI): m/z=502.162 [M+H]+.

1H NMR (600 MHz, DMSO-d6) δ ppm 3.79 (br d, J=5.9 Hz, 2H) 4.17-4.22 (m, 1H) 4.29 (d, J=6.7 Hz, 2H) 7.29-7.35 (m, 2H) 7.42 (t, J=7.4 Hz, 2H) 7.54-7.60 (m, 2H) 7.61-7.70 (m, 4H) 7.71-7.76 (m, 2H) 7.77 (br dJ,=8.0 Hz, 1H) 7.89 (d, J=7.7 Hz, 2H) 7.97 (d, J=7.6 Hz, 1H) 10.04 (s, 1H)

Intermediate 3

9H-fluoren-9-ylmethyl N-[[2-(3-formylphenyl)-5-(trifluoromethyl)phenyl]methyl]carbamate

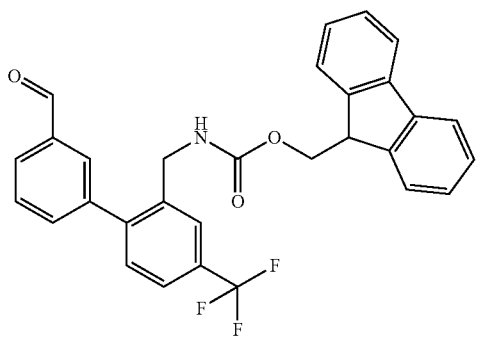 [SMILES: O=Cc1cccc(-c2ccc(C(F)(F)F)cc2CNC(=O)OCC2c3ccccc3-c3ccccc32)c1]

A microwave reaction vessel was charged with (3-(methoxycarbonyl)phenyl)boronic acid (540 mg, 3 mmol), 2-bromo-5-(trifluoromethyl)benzonitrile (500 mg, 2 mmol), 2-Dicyclohexylphosphino-2',6'-dimethoxybiphenyl (82 mg, 0.2 mmol), potassium phosphate tribasic (1.27 g, 6 mmol) and palladium(II) acetate (22.5 mg, 0.1 mmol) and was sealed. It was put under vacuum and filled with argon (3× repeated). Then the degassed toluene was added and the suspension was stirred at 80° C. for 2 hours. The reaction mixture was then allowed to cool to room temperature, diluted with 5 ml EtOAc and filtered through a thin bed of silica (0.3-0.5 mm) and eluted/washed with EtOAc (ca. 40 ml) and concentrated under reduced pressure. After SiO2 flash chromatography, methyl 2'-cyano-4'-(trifluoromethyl)[1,1'-biphenyl]-3-carboxylate was obtained as a off-white, crystalline solid (567 mg, 92.9%). MS (ESI): m/z=306.2 [M+H]+.

6.95 ml 1M LiAlH$_4$ in THF was diluted with 7 ml THF, anhydrous, and put in a dried flask under Ar. It was cooled to −20° C. and then the dissolved methyl 2'-cyano-4'-(trifluoromethyl)-[1,1'-biphenyl]-3-carboxylate (in 11 ml THF, anh.) was added dropwise within ca. 1 hour, the temperature was kept between −18 and −20° C. The ice bath was removed, the reaction was allowed to warm to room temp (ca. 30 min) and let stir for additional 15 min. The reaction was quenched with ca. 15 g ice. 3 ml of 1 M NaOH, 30 ml sat. Na—K-Tartrate and 30 ml EtOAc were added. The aqueous solution was extracted with EtOAc (3×), the organic phases were pooled, washed with brine, dried over MgSO4 and concentrated in vacuo to yield crude (2'-(aminomethyl)-4'-(trifluoromethyl)-[1,1'-biphenyl]-3-yl)methanol. MS (ESI): m/z=282.2 [M+H]+.

526 mg (1.87 mmol) (2'-(aminomethyl)-4'-(trifluoromethyl)-[1,1'-biphenyl]-3-yl)methanol was dissolved in MeOH and pyridine and stirred at room temp. 694 mg (2.06 mmol) Fmoc-OSu was dissolved in 2.5 ml THF and added within 30 min to the stirred reaction. After 1-2 h turbidity was observed, but after stirring overnight the reaction solution was clear again. 30 ml EtOAc and 30 ml citric acid (10%) were added to extract the product. The aq phase was extracted a second and third time with 30 ml EtOAc, the two combined organic phases were washed with Brine, dried over MgSO4 and rotavapped to dryness. It was redissolved in EtOAc and put on SiO2 for flash chromatography to yield 9H-fluoren-9-ylmethyl N-[[2-[3-(hydroxymethyl)phenyl]-5-(trifluoromethyl)phenyl]methyl]carbamate (520 mg, 55.2%). MS (ESI): m/z=504.43 [M+1-1]+.

520 mg (1.03 mmol) 9H-fluoren-9-ylmethyl N-[[2-[3-(hydroxymethyl)phenyl]-5-(trifluoromethyl)phenyl]methyl]carbamate was dissolved in THF and DCM and the 1.8 g (20.7 mmol) MnO2 was added. After stirring over night the MnO2 was filtered away, thoroughly washed with THF and the solvent of the filtrate was removed in vacuo. Purification by SiO2 flash chromatography to yield 9H-fluoren-9-ylmethyl N-[[2-(3-formylphenyl)-5-(trifluoromethyl)phenyl]methyl]carbamate as a white solid (225 mg, 43.4%). MS (ER): m/z=502.4 [M+H]+.

1H NMR (400 MHz, CDCl3) δ ppm 4.06 (t, 1H) 4.26-4.35 (m, 4H) 4.89 (m, 1H) 7.18-7.35 (m, 6H) 7.45-7.57 (m, 4H) 7.65-7.75 (m, 4H), 7.84-7.87 (m, 1H), 9.95 (s, 1H)

Intermediate 4 (9H-fluoren-9-yl)methyl ((3'-formyl-6-methyl-[1,1'-biphenyl]-2-yl)methyl)carbamate

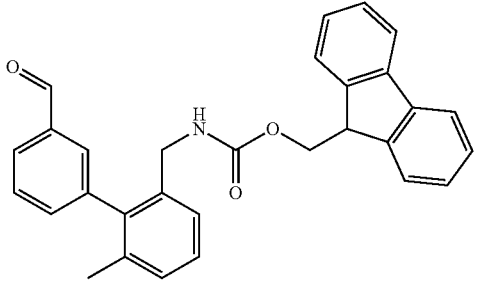 [SMILES: Cc1cccc(CNC(=O)OCC2c3ccccc3-c3ccccc32)c1-c1cccc(C=O)c1]

A microwave reaction vessel was charged with (3-(methoxycarbonyl)phenyl)boronic acid (540 mg, 3 mmol), 2-bromo-3-methylbenzonitrile (392 mg, 2 mmol), 2-Dicyclohexylphosphino-2',6'-dimethoxybiphenyl (82 mg, 0.2 mmol), potassium phosphate tribasic (1.27 g, 6 mmol), and palladium(II) acetate (22.5 mg, 0.1 mmol) and was sealed. It was put under vacuum and filled with argon (3× repeated). Then the degassed toluene was added and the suspension was stirred at 80° C. for 2 hours. The reaction mixture was then allowed to cool to room temperature, diluted with 5 ml EtOAc and filtered through a thin bed of silica (0.3-0.5 mm) and eluted/washed with EtOAc (ca. 40 ml) and concentrated under reduced pressure. After SiO2 flash chromatography, methyl 2'-cyano-6'-methyl-[1,1'-biphenyl]-3-carboxylate was obtained as a off-white, crystalline solid (489 mg, 97.3%). MS (ER): m/z=252.2 [M+H]+.

1H NMR (400 MHz, CDCl3) δ ppm 2.17 (s, 3H), 3.9 (s, 3H), 7.38 (t, 1H, J=10.2 Hz), 7.37-7.60 (m, 4H), 7.98 (dd, 1H, J=0.8 Hz), 8.11 (m, 1H) 2.75 ml 1M LiAlH$_4$ in THF were diluted with 3 ml THF, anhydrous, and put in a dried flask under Ar. It was cooled to −20° C. and then the dissolved methyl 2'-cyano-6'-methyl-[1,1'-biphenyl]-3-carboxylate (173 mg, 0.68 mmol, in 6 ml THF, anh.) was added dropwise within ca. 1 hour, the temperature was kept between −18 and −20° C. The ice bath was removed, the reaction was allowed to warm to room temp (ca. 30 min) and let stir for additional 15 min. The reaction was quenched with ca. 5 g ice. 3 ml of 1 M NaOH, 30 ml sat. Na—K-Tartrate and 30 ml EtOAc were added. The aqueous solution was extracted with EtOAc (3×), the organic phases were pooled, washed with brine, dried over MgSO4 and concentrated in vacuo. No purification before the next step. (2'-(aminomethyl)-6'-methyl[1,1'-biphenyl]-3-yl)methanol, 150 mg, 95.9%, MS (ESI): m/z=228.2 [M+H]+(2'-(aminomethyl)-6'-methyl[1,1'-biphenyl]-3-yl)methanol (150 mg, 0.66 mmol) was dissolved in MeOH (6.2 ml) and pyridine (160 µl, 1.98 mmol) and stirred at room temp. Fmoc-OSu (245 mg, 0.66 mmol) was added to the stirred reaction. After 1-2 h turbidity was observed, but after stirring overnight the reaction solution was clear again. 30 ml EtOAc and 30 ml citric acid (10%) were added to extract the product. The aq phase was extracted a second and third time with 30 ml EtOAc, the two combined organic phases were washed with brine, dried over MgSO4 and rotavapped to dryness. The residue was redissolved in EtOAc and put on SiO2 for flash chromatography to yield (9H-fluoren-9-yl)methyl ((3'-(hydroxymethyl)-6-methyl-[1,1'-biphenyl]-2-yl)methyl)carbamate (67 mg, 22.6%) MS (ER): m/z=450.29 [M+H]+.

(9H-fluoren-9-yl)methyl ((3'-(hydroxymethyl)-6-methyl-[1,1'-biphenyl]-2-yl)methyl)carbamate (67 mg, 0.149 mmol) was dissolved in THF and DCM and MnO2 (259 mg, 2.98 mmol) was added. After stirring over night only product observed by TLC. The MnO2 was then filtered away, thoroughly washed with THF and the solvent of the filtrate was removed in vacuo to yield (9H-fluoren-9-yl)methyl ((3'-formyl-6-methyl-[1,1'-biphenyl]-2-yl)methyl)carbamate (35 mg, 52.5%). MS (ESI): m/z=448.3 [M+H]+.

Intermediate 5

9H-fluoren-9-ylmethyl N-[[5-chloro-2-(3-formylphenyl)phenyl]methyl]carbamate

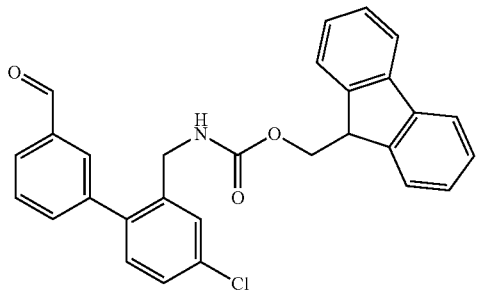 [SMILES: O=Cc1cccc(-c2ccc(Cl)cc2CNC(=O)OCC2c3ccccc3-c3ccccc32)c1]

A microwave reaction vessel was charged with (3-(ethoxycarbonyl)phenyl)boronic acid (427 mg, 2.2 mmol), 2-bromo-5-chlorobenzonitrile (433 mg, 2 mmol), 2-Dicyclohexylphosphino-2',6'-dimethoxybiphenyl (82 mg, 0.2 mmol), potassium phosphate tribasic (1.27 g, 6 mmol), and palladium(II) acetate (22.5 mg, 0.1 mmol) and was sealed. It was put under vacuum and filled with argon (3× repeated). Then the degassed toluene was added and the suspension was stirred at 80° C. for 2 hours. The reaction mixture was then allowed to cool to room temperature, diluted with 5 ml EtOAc and filtered through a thin bed of silica (0.3-0.5 mm) and eluted/washed with EtOAc (ca. 40 ml) and concentrated under reduced pressure. After SiO2 flash chromatography, ethyl 4'-chloro-2'-cyano-[1,1'-biphenyl]-3-carboxylate was obtained as a off-white, crystalline solid (481 mg, 84.2%). MS (ER): m/z=286.1 [M+H]+.

1H NMR (400 MHz, CDCl3) δ ppm 1.34 (t, 3H, J=9.2 Hz), 4.34 (q, 2H, J=9.2 Hz), 7.42 (d, 1H, J=11.2 Hz), 7.48-7.59 (m, 2H) 7.66-7.70 (m, 2H), 8.05-8.11 (m, 2H) 6.3 ml 1M LiAlH4 in THF were diluted with 7 ml THF, anhydrous, and put in a dried flask under Ar. It was cooled to −20° C. and then the dissolved ethyl 4'-chloro-2'-cyano-[1,1'-biphenyl]-3-carboxylate (450 mg, 1.57 mmol, in 10 ml THF, anh.) was added dropwise within ca. 1 hour, the temperature was kept between −18 and −20° C. The ice bath was removed, the reaction was allowed to warm to room temp (ca. 30 min) and let stir for additional 15 min. The reaction was quenched with 5 g ice. 3 ml of 1 M NaOH, 30 ml sat. Na—K-Tartrate and 30 ml EtOAc were added. The aqueous solution was extracted with EtOAc (3×), the organic phases were pooled, washed with brine, dried over MgSO4 and concentrated in vacuo. No purification before the next step. (2'-(aminomethyl)-4'-chloro-[1,1'-biphenyl]-3-yl)methanol, 244 mg, 62.6%, MS (ESI): m/z=248.2 [M+H]+.

(2'-(aminomethyl)-4'-chloro-[1,1'-biphenyl]-3-yl)methanol (291 mg, 1.17 mmol) was dissolved in MeOH (12.1 ml) and pyridine (0.285 ml, 3.52 mmol) and stirred at room temp.

Fmoc-OSu (436 mg, 1.29 mmol) was added to the reaction. After stirring overnight, 30 ml EtOAc and 30 ml citric acid (10%) were added to extract the product. The aq phase was extracted a second and third time with 30 ml EtOAc, the two combined organic phases were washed with Brine, dried over MgSO4 and rotavapped to dryness. It was redissolved in EtOAc and put on SiO2 for flash chromatography to yield (9H-fluoren-9-yl)methyl 44-chloro-Y-(hydroxymethyl)-[1,1'-biphenyl]-2-yl)methyl)carbamate (160 mg, 29%). MS (ER): m/z=470.28 [M+H]+.

(9H-fluoren-9-yl)methyl 44-chloro-3'-(hydroxymethyl)-[1,1'-biphenyl]-2-yl)methyl)carbamate (160 mg, 0.34 mmol) was dissolved in THF and DCM 1:1, 23.6 ml, and MnO2 (592 mg, 6.81 mmol) was added. After stirring over night only product observed. The MnO2 was then filtered away, thoroughly washed with THF and the solvent of the filtrate was removed in vacuo. Purification using SiO2 flash chromatography yielded 9H-fluoren-9-ylmethyl N-[[5-chloro-2-(3-formylphenyl)phenyl]methyl]carbamate (96 mg, 60.3%). MS (ESI): m/z=468.29 [M+H]+.

Intermediate 6

9H-fluoren-9-ylmethyl N-[[2-chloro-6-(3-formylphenyl)phenyl]methyl]carbamate

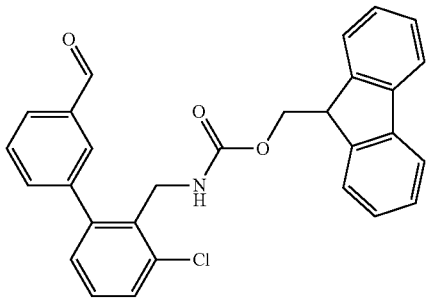 [SMILES: O=Cc1cccc(-c2cccc(Cl)c2CNC(=O)OCC2c3ccccc3-c3ccccc32)c1]

To a solution of (3-(ethoxycarbonyl)phenyl)boronic acid (350 mg, 1.8 mmol, Eq: 1.3) in THF (5 mL) was added 2-bromo-6-chlorobenzonitrile (300 mg, 1.39 mmol, Eq: 1) and potassium fluoride (242 mg, 4.16 mmol, Eq: 3). The reaction mixture was degassed under a slight argon flush in an ultrasonic bath for 15 minutes. palladium(II)acetate (6.22 mg, 27.7 µmol, Eq: 0.02) and (2-biphenyl)di-tert-butylphosphine (16.5 mg, 55.4 µmol, Eq: 0.04) was added. The reaction mixture was stirred for 18 hours at 50° C. The reaction mixture was poured on 30 mL water and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield ethyl 3-(3-chloro-2-cyanophenyl)benzoate as a white foam (188 mg, 44.4%). GC-MS: m/z=285.1

To a solution of LiAlH4 1M in THF (4.01 mL, 4.01 mmol, Eq: 4) diluted with dry THF (7 mL) was added at −20° C. dropwise a solution of ethyl 3-(3-chloro-2-cyanophenyl)benzoate (244 mg, 1 mmol, Eq: 1) in dry THF (7 mL) within one hour. The reaction mixture was stirred for 2 hours at room temperature. The reaction mixture was poured on 30 mL saturated aqueous sodium potassium tartrate solution (containing ca. 2 mL aqueous 1N NaOH) and 30 mL EtOAc and the layers were separated. The aqueous layer was extracted a second time with 30 mL EtOAc. The organic layers were washed with 30 mL brine, dried over MgSO4, filtered and concentrated under vacuum to yield [3-[2-(aminomethyl)-3-chlorophenyl]phenyl]methanol as a yellow foam (230 mg, 92.7%). MS (ER): m/z=248.085 [M+H]+.

To a solution of [3-[2-(aminomethyl)-3-chlorophenyl]phenyl]methanol (223 mg, 900 µmol, Eq: 1) in MeOH (8 mL) was added pyridine (285 mg, 290 µL, 3.6 mmol, Eq: 4) and 9-fluorenylmethyl-N-succinimidyl carbonate (364 mg, 1.08 mmol, Eq: 1.2). The suspension was stirred for 48 hours at room temperature. The reaction mixture was poured on 30 mL 10% aqueous citric acid solution and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield 9H-fluoren-9-ylmethyl N-[[2-chloro-6-[3-(hydroxymethyl)phenyl]phenyl]methyl]carbamate as a white foam (188 mg, 44.4%). MS (ESI): m/z=470.152 [M+H]+.

To a solution of 9H-fluoren-9-ylmethyl N-[[2-chloro-6-[3-(hydroxymethyl)phenyl]phenyl]methyl]carbamate (178 mg, 379 µmol, Eq: 1) in DCM (5 mL) and THF (5 mL) was added manganese(IV) oxide activated (659 mg, 7.58 mmol, Eq: 20). The reaction mixture was stirred for 3 hours at room temperature. The reaction mixture was filtered over a pad of dicalite and washed with EtOAc. The filtrate was concentrated under vacuum. The residue was purified by silica gel chromatography to yield 9H-fluoren-9-ylmethyl N-[[2-chloro-6-(3-formylphenyl)phenyl]methyl]carbamate as a white foam (129 mg, 72.8%). MS (ER): m/z=468.14 [M+H]+.

1H NMR (600 MHz, DMSO-d6) δ ppm 4.14 (d, J=4.4 Hz, 2H) 4.15-4.19 (m, 1H) 4.20-4.23 (m, 2H) 7.28 (d, J=7.2 Hz, 1H) 7.31 (t, J=7.5 Hz, 2H) 7.41 (0=7.5 Hz, 2H) 7.45 (t, J=7.9 Hz, 1H) 7.57 (d, J=8.0 Hz, 1H) 7.62-7.68 (m, 2H) 7.69 (d, J=7.5 Hz, 2H) 7.75 (br d, J=7.5 Hz, 1H) 7.86-7.90 (m, 2H) 7.91-7.93 (m, 1H) 7.94 (br d, J=1.3 Hz, 1H) 10.01 (s, 1H)

Intermediate 7

9H-fluoren-9-ylmethyl N-[[2-(3-formylphenyl)-5-methylphenyl]methyl]carbamate

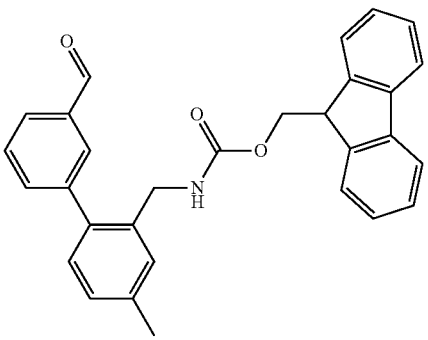 [SMILES: Cc1ccc(-c2cccc(C=O)c2)c(CNC(=O)OCC2c3ccccc3-c3ccccc32)c1]

To a solution of (3-(ethoxycarbonyl)phenyl)boronic acid (386 mg, 1.99 mmol, Eq: 1.3) in THF (5 mL) was added 2-bromo-5-methylbenzonitrile (300 mg, 1.53 mmol, Eq: 1) and potassium fluoride (267 mg, 4.59 mmol, Eq: 3). The reaction mixture was degassed under a slight argon flush in an ultrasonic bath for 15 minutes. palladium(II)acetate (6.87 mg, 30.6 µmol, Eq: 0.02) and (2-biphenyl)di-tert-butylphosphine (18.3 mg, 61.2 µmol, Eq: 0.04) was added. The reaction mixture was stirred for 18 hours at 50° C. The reaction mixture was poured on 30 mL water and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield ethyl 3-(2-cyano-4-methylphenyl)benzoate as a white solid (383 mg, 94.3%). MS (ESI): m/z=266.118 [M+H]+.

To a solution of LiAlH4 1M in THF (6 mL, 6 mmol, Eq: 4) diluted with dry THF (7 mL) was added at −20° C. dropwise a solution of ethyl 3-(2-cyano-4-methylphenyl)benzoate (335 mg, 1.5 mmol, Eq: 1) in dry THF (7 mL) within one hour. The reaction mixture was stirred for 2 hours at room temperature. The reaction mixture was poured on 30 mL saturated aqueous sodium potassium tartrate solution (containing ca. 2 mL aqueous 1N NaOH) and 30 mL EtOAc and the layers were separated. The aqueous layer was extracted a second time with 30 mL EtOAc. The organic layers were washed with 30 mL brine, dried over MgSO4, filtered and concentrated under vacuum to yield [3-[2-(aminomethyl)-4-methylphenyl]phenyl]methanol as a light yellow foam (304 mg, 89.1%). MS (ER): m/z=228.14 [M+H]+.

To a solution of [3-[2-(aminomethyl)-4-methylphenyl]phenyl]methanol (298 mg, 1.31 mmol, Eq: 1) in MeOH (8 mL) was added pyridine (415 mg, 422 µL, 5.24 mmol, Eq: 4) and 9-fluorenylmethyl-N-succinimidyl carbonate (531 mg, 1.57 mmol, Eq: 1.2). The suspension was stirred for 24 hours at room temperature. The reaction mixture was poured on 30 mL 10% aqueous citric acid solution and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield 9H-fluoren- 9-ylmethyl N-[[2-[3-(hydroxymethyl)phenyl]-5-methylphenyl]methyl]carbamate as a colorless oil (187 mg, 31.7%). MS (ER): m/z=450.206 [M+H]+.

To a solution of 9H-fluoren-9-ylmethyl N-[[2-[3-(hydroxymethyl)phenyl]-5-methylphenyl]methyl]carbamate (174 mg, 387 μmol, Eq: 1) in DCM (5 mL) and THF (5 mL) was added manganese(IV) oxide activated (673 mg, 7.74 mmol, Eq: 20). The reaction mixture was stirred for 3 hours at room temperature. The reaction mixture was filtered over a pad of dicalite and washed with EtOAc. The filtrate was concentrated under vacuum. The residue was purified by silica gel chromatography to yield 9H-fluoren-9-ylmethyl N-[[2-(3-formylphenyl)-5-methylphenyl]methyl]carbamate as a white foam (40 mg, 23.1%). MS (ESI): m/z=448.191 [M+H]+.

1H NMR (600 MHz, DMSO-d6) δ ppm 2.35 (s, 3H) 4.12 (d, J=5.8 Hz, 2H) 4.18-4.23 (m, 1H) 4.28 (d, J=7.2 Hz, 2H) 7.12-7.19 (m, 2H) 7.23 (s, 1H) 7.32 (t, J=7.3 Hz, 2H) 7.42 (t, J=7.4 Hz, 2H) 7.61-7.66 (m, 1H) 7.69 (br d, J=7.5 Hz, 3H) 7.80 (br t, J=5.9 Hz, 1H) 7.85 (s, 1H) 7.89 (d, J=7.6 Hz, 3H) 10.04 (s, 1H)

Intermediate 8

9H-fluoren-9-ylmethyl N-[[2-(3-formylphenyl)-4-(trifluoromethyl)phenyl]methyl]carbamate

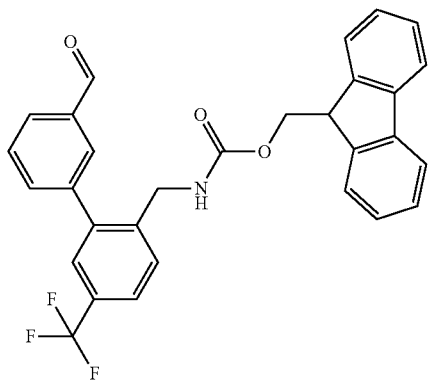 [SMILES: O=Cc1cccc(-c2cc(C(F)(F)F)ccc2CNC(=O)OCC2c3ccccc3-c3ccccc32)c1]

To a solution of (3-(methoxycarbonyl)phenyl)boronic acid (324 mg, 1.8 mmol, Eq: 1.5) in toluene (5 mL) and water (500 μL) was added 2-bromo-4-(trifluoromethyl)benzonitrile (300 mg, 1.2 mmol, Eq: 1) and SPhos (49.3 mg, 120 μmol, Eq: 0.1) and potassium phosphate tribasic anhydrous (764 mg, 3.6 mmol, Eq: 3) and palladium(II)acetate (13.5 mg, 60 μmol, Eq: 0.05). The reaction mixture was stirred for 6 hours at 110° C. The reaction mixture was poured on 30 mL 10% aqueous NaHCO3 solution and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield methyl 3-[2-cyano-5-(trifluoromethyl)phenyl]benzoate (338 mg, 73.8%). GCMS (EI): m/z=305.1 [M+H]+.

To a solution of LiAlH4 1M in THF (4.06 mL, 4.06 mmol, Eq: 4) in dry THF (7 mL) was added at −20° C. dropwise a solution of methyl 3-[2-cyano-5-(trifluoromethyl)phenyl] benzoate (310 mg, 1.02 mmol, Eq: 1) in dry THF (7 mL) within 45 minutes. The reaction mixture was stirred for 18 hours. The reaction mixture was poured on 30 mL saturated aqueous sodium potassium tartrate solution (containing ca. 2 mL aqueous 1N NaOH) and 30 mL EtOAc and the layers were separated. The aqueous layer was extracted a second time with 30 mL EtOAc. The organic layers were washed with 30 mL brine, dried over MgSO4, filtered and concentrated under vacuum to yield [3-[2-(aminomethyl)-5-(trifluoromethyl)phenyl]phenyl]methanol as a light yellow solid (147 mg, 50.8%). MS (ESI): m/z=282.2 [M+H]+.

To a solution of [3-[2-(aminomethyl)-5-(trifluoromethyl)phenyl]phenyl]methanol (290 mg, 1.03 mmol, Eq: 1) in MeOH (8 mL) was added pyridine (326 mg, 332 μL, 4.12 mmol, Eq: 4) and 9-fluorenylmethyl-N-succinimidyl carbonate (417 mg, 1.24 mmol, Eq: 1.2). The suspension was stirred for 18 hours at room temperature. The reaction mixture was poured on 30 mL 10% aqueous citric acid solution and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography to yield 9H-fluoren-9-ylmethyl N-[[2-[3-(hydroxymethyl)phenyl]-4-(trifluoromethyl)phenyl]methyl]carbamate as a white solid (309 mg, 59.5 mg). MS (ER): m/z=504.18 [M+H]+.

To a solution of 9H-fluoren-9-ylmethyl N-[[2-[3-(hydroxymethyl)phenyl]-4-(trifluoromethyl)phenyl]methyl] carbamate (299 mg, 594 μmol, Eq: 1) in DCM (7 mL) and THF (7 mL) was added manganese(IV) oxide activated (1.03 g, 11.9 mmol, Eq: 20). The reaction mixture was stirred for 3 hours at room temperature. The reaction mixture was filtered over a pad of dicalite and washed with EtOAc. The filtrate was concentrated under vacuum. The residue was purified by silica gel chromatography to yield 9H-fluoren-9-ylmethyl N-[[2-(3-formylphenyl)-4-(trifluoromethyl) phenyl]methyl]carbamate as a white solid (169 mg, 56.7%). MS (ESI): m/z=502.16 [M+H]+.

1H NMR (600 MHz, DMSO-d6) δ ppm 10.07 (s, 1H), 7.92-7.98 (m, 2H), 7.87-7.92 (m, 3H), 7.76-7.81 (m, 2H), 7.65-7.72 (m, 3H), 7.56-7.60 (m, 2H), 7.42 (t, J=7.4 Hz, 2H), 7.30-7.35 (m, 2H), 4.32 (d, J=6.9 Hz, 2H), 4.15-4.22 (m, 3H)

Intermediate 9

9H-fluoren-9-ylmethyl N-[[2-(3-formylphenyl)-5-methoxyphenyl]methyl]carbamate

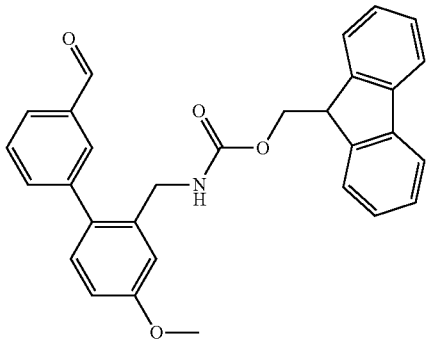 [SMILES: COc1ccc(-c2cccc(C=O)c2)c(CNC(=O)OCC2c3ccccc3-c3ccccc32)c1]

To a solution of 2-bromo-5-methoxybenzaldehyde (1.08 g, 5 mmol, Eq: 1) and THF (20.8 mL) was added 2-methylpropane-2-sulfinamide (606 mg, 5 mmol, Eq: 1) and titanium(IV) ethoxide (3.42 g, 3.14 mL, 15 mmol, Eq: 3). The reaction mixture was then heated to 70° C. and stirred for 3 hours. To the reaction mixture were added 20 mL brine and then it was filtered and washed with 50 mL EtOAc and the layers were separated. The organic layers were washed with 30 mL brine, dried over MgSO4, filtered and concentrated under vacuum to yield N-[(2-bromo-5-methoxyphenyl)methylidene]-2-methylpropane-2-sulfinamide (1400 mg, 88%).

To a solution of N-[(2-bromo-5-methoxyphenyl)methylidene]-2-methylpropane-2-sulfinamide (700 mg, 2.2 mmol, Eq: 1) in dioxane (4 mL) and water (400 µL) was added (3-(methoxycarbonyl)phenyl)boronic acid (475 mg, 2.64 mmol, Eq: 1.2) and potassium carbonate (912 mg, 6.6 mmol, Eq: 3) and 1,1'-bis(diphenylphosphino)ferrocene palladium (II) chloride (80.5 mg, 110 µmol, Eq: 0.05). The reaction mixture was then stirred for 4 hours at 80° C. The reaction mixture was poured on 30 mL 10% aqueous NaHCO3 solution and 30 mL EtOAc and the layers were separated. The aqueous layer was extracted a second time with 30 mL EtOAc. The organic layers were, dried over MgSO4, filtered and concentrated under vacuum. The residue was purified by silica gel chromatography, methyl 3-[2-[tert-butylsulfinyliminomethyl]-4-methoxyphenyl]benzoate was obtained as a light yellow oil (729 mg, 88.7%).

1H NMR (300 MHz, CHLOROFORM-d) δ ppm 1.25 (s, 9H) 3.92 (d, 6H) 7.13 (dd, J=8.48, 2.83 Hz, 1H) 7.35 (d, J=8.48 Hz, 1H) 7.43-7.56 (m, 2H) 7.66 (d, J=2.83 Hz, 1H) 7.98 (t, J=1.41 Hz, 1H) 8.01-8.10 (m, 1H) 8.53 (s, 1H)

To a solution of LiAlH4 1M in THF (2.81 mL, 2.81 mmol, Eq: 3) diluted with dry THF (7 mL) was added at −20° C. dropwise a solution of methyl 3-[2-[tert-butylsulfinyliminomethyl]-4-methoxyphenyl]benzoate (350 mg, 937 µmol, Eq: 1) in dry THF (7 mL) within 30 minutes. The reaction mixture was stirred for 1.5 hours. The reaction mixture was poured on 30 mL saturated aqueous sodium potassium tartrate solution (containing ca. 2 mL aqueous 1N NaOH) and 30 mL EtOAc and the layers were separated. The aqueous layer was extracted a second time with 30 mL EtOAc. The organic layers were washed with 30 mL brine, dried over MgSO4, filtered and concentrated under vacuum. N-[[2-3-(hydroxymethyl)phenyl]-5-methoxyphenyl]methyl]-2-methylpropane-2-sulfinamide was obtained as a colorless oil (326 mg, 100%). MS (ER): m/z=348.16 [M+H]+.

To a solution of N-[[2-[3-(hydroxymethyl)phenyl]-5-methoxyphenyl]methyl]-2-methylpropane-2-sulfinamide (335 mg, 0.964 mmol, Eq: 1) in dioxane (5 mL) was added HCl 4M in dioxane (1.75 mL, 7 mmol, Eq: 7.26). The reaction mixture was stirred for 4 hours at room temperature. The reaction mixture was concentrated under vacuum to yield [3-[2-(aminomethyl)-4-methoxyphenyl]phenyl]methanol hydrochloride as a white solid (255 mg, 94.6%). MS (ESI): m/z=244.13 [M+H]+.

To a solution of [3-[2-(aminomethyl)-4-methoxyphenyl]phenyl]methanol hydrochloride (255 mg, 911 µmol, Eq: 1) in MeOH (8 mL) was added pyridine (433 mg, 441 µL, 5.47 mmol, Eq: 6) and 9-fluorenylmethyl-N-succinimidyl carbonate (369 mg, 1.09 mmol, Eq: 1.2). The suspension was stirred for 2.5 hours at room temperature. The reaction mixture was poured on 30 mL 10% aqueous citric acid solution and 30 mL EtOAc and the layers were separated. The aqueous layer was extracted a second time with 30 mL EtOAc. The organic layers were washed with 30 mL brine, dried over MgSO4, filtered and concentrated under vacuum. The residue was purified by silica gel chromatography, 9H-fluoren-9-ylmethyl N-[[2-[3-(hydroxymethyl)phenyl]-5-methoxyphenyl]methyl]carbamate was obtained as light yellow foam (164 mg, 38.6%) MS (ESI): m/z=466.20 [M+1-1]+.

To a solution of 9H-fluoren-9-ylmethyl N-[[2-[3-(hydroxymethyl)phenyl]-5-methoxyphenyl]methyl]carbamate (160 mg, 344 µmol, Eq: 1) in DCM (7 mL) and THF (7 mL) was added manganese(IV) oxide activated (598 mg, 6.87 mmol, Eq: 20). The reaction mixture was stirred for 2 hours at room temperature. The reaction mixture was filtered over a pad of dicalite and washed with EtOAc. The filtrate was concentrated under vacuum. 9H-fluoren-9-ylmethyl N-[[2-(3-formylphenyl)-5-methoxyphenyl]methyl]carbamate was obtained as an off-white solid (138 mg, 86.6%). MS (ESI): m/z=464.18 [M+H]+.

1H NMR (600 MHz, DMSO-d6) δ ppm 10.05 (s, 1H), 7.80-7.92 (m, 5H), 7.69 (d, J=7.5 Hz, 2H), 7.66-7.71 (m, 1H), 7.62-7.66 (m, 1H), 7.38-7.47 (m, 2H), 7.32 (t, J=7.4 Hz, 2H), 7.21 (d, J=8.5 Hz, 1H), 7.01 (d, J=2.3 Hz, 1H), 6.95 (dd, J=8.5, 2.5 Hz, 1H), 4.28 (d, J=7.1 Hz, 2H), 4.19-4.23 (m, 1H), 4.13 (d, J=5.9 Hz, 2H), 3.79 (s, 3H)

Intermediate 10

9H-fluoren-9-ylmethyl N-[[2-(2-fluoro-3-formylphenyl)phenyl]methyl]carbamate

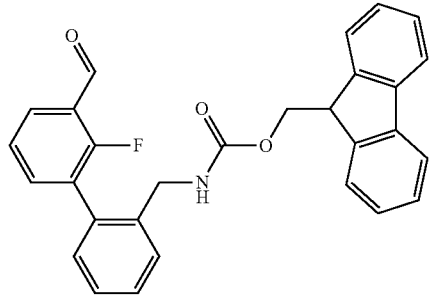 [SMILES: O=Cc1cccc(-c2ccccc2CNC(=O)OCC2c3ccccc3-c3ccccc32)c1F]

To a solution of (2-bromophenyl)methanamine (2 g, 10.7 mmol, Eq: 1) in MeOH (60 ml) was added pyridine (2.55 g, 2.6 mL, 32.2 mmol, Eq: 3) and 9-fluorenylmethyl-N-succinimidyl carbonate (3.63 g, 10.7 mmol, Eq: 1). A very thick precipitation occurred. MeOH (80 ml) was added. The suspension was stirred over night at room temperature. The reaction mixture was poured on 230 mL 10% aqueous NaHCO3 solution and 230 mL EtOAc and the layers were separated. The aqueous layer was extracted a second time with 230 mL EtOAc. The organic layers were washed with 230 mL water and 230 mL brine, dried over MgSO4, filtered and concentrated under vacuum. The yellow solid was dissolved in 180 mL MeOH at reflux. The yellow solution was allowed to cool to room temperature and then stirred for 30 minutes at 0° C. The white solid was filtrated and dried under vacuum to yield 9H-fluoren-9-ylmethyl N-[(2-bromophenyl)methyl]carbamate (2.21 g, 50.3%). MS (ESI): m/z=410.06 [M+H]+.

To a solution of 9H-fluoren-9-yl)methyl 2-bromobenzyl-carbamate (800 mg, 1.96 mmol, Eq: 1) in degassed THF (10 mL) was added (2-fluoro-3-(methoxycarbonyl)phenyl)boronic acid (465 mg, 2.35 mmol, Eq: 1.20) and potassium fluoride (342 mg, 5.88 mmol, Eq: 3) and palladium(II) acetate (8.8 mg, 39.2 µmol, Eq: 0.02) and (2-biphenyl)di-tert-butylphosphine (23.4 mg, 78.4 µmol, Eq: 0.04) was added. The reaction mixture was stirred for 6 hours at 50° C. The reaction mixture was poured on 30 mL 10% aqueous citric acid solution and 30 mL EtOAc and the layers were separated. The aqueous layer was extracted a second time with 20 mL EtOAc. The organic layers were washed with 20 mL brine, dried over MgSO4, filtered and concentrated under vacuum. The residue was purified by silica gel chromatography to yield methyl 3-[2-[(9H-fluoren-9-ylmethoxycarbonylamino)methyl]phenyl]-2-fluorobenzoate as light yellow oil (354 mg, 37.5%). MS (ER): m/z=482.178 [M+H]+.

To a solution of methyl 3-[2-[(9H-fluoren-9-ylmethoxycarbonylamino)methyl]phenyl]-2-fluorobenzoate (215 mg, 447 µmol, Eq: 1) in dry THF (4 mL) was added dropwise diisobutylaluminiumhydide solution 1M in THF (1.12 mL, 1.12 mmol, Eq: 2.5) at 0° C. The reaction mixture was stirred for 1 hour at room temperature. TLC shows about 50% conversion. diisobutylaluminiumhydide solution 1M in THF (558 µL, 558 µmol, Eq: 1.25) was added dropwise at room temperature. The reaction mixture was stirred for 30 minutes at room temperature. TLC shows still starting material. diisobutylaluminiumhydide solution 1M in THF (558 µL, 558 µmol, Eq: 1.25) was added dropwise at room temperature. The reaction mixture was stirred for 30 minutes at room temperature. TLC shows complete conversion of the starting material. The reaction mixture was poured on 30 mL saturated aqueous sodium potassium tartrate solution and 30 mL EtOAc. The layers were filtered over a pad of dicalite and the layers were separated. The aqueous layer was extracted a second time with 30 mL EtOAc. The organic layers were washed with 30 mL brine, dried over MgSO4, filtered and concentrated under vacuum. The product was used crude in the next step. 9H-fluoren-9-ylmethyl N-[[2-[2-fluoro-3-(hydroxymethyl)phenyl]phenyl]methyl]carbamate was obtained as a light yellow oil (221 mg, 109%). MS (ESI): m/z=454.181 [M+H]+.

To a solution of 9H-fluoren-9-ylmethyl N-[[2-[2-fluoro-3-(hydroxymethyl)phenyl]phenyl]methyl]carbamate (210 mg, 463 µmol, Eq: 1) in DCM (4 mL) and THF (4 mL) was added manganese(IV) oxide activated (805 mg, 9.26 mmol, Eq: 20). The reaction mixture was stirred for 3 hours at room temperature. The reaction mixture was filtered over a pad of dicalite and washed with EtOAc. The filtrate was concentrated under vacuum. The residue was purified by silica gel chromatography, 9H-fluoren-9-ylmethyl N-[[2-(2-fluoro-3-formylphenyl)phenyl]methyl]carbamate was obtained as a light yellow foam (122 mg, 58.4%). MS (ESI): m/z=452.165 [M+H]+.

1H NMR (600 MHz, DMSO-d6) δ ppm 10.25 (s, 1H), 7.82-7.94 (m, 4H), 7.75 (br t, J=5.9 Hz, 1H), 7.67 (br d, J=7.4 Hz, 3H), 7.21-7.51 (m, 12H), 4.26 (br d, J=6.5 Hz, 2H), 4.14-4.21 (m, 1H), 3.95-4.10 (m, 3H)

Intermediate 11

9H-fluoren-9-ylmethyl N-[[5-chloro-2-(4-formylpyridin-2-yl)phenyl]methyl]carbamate

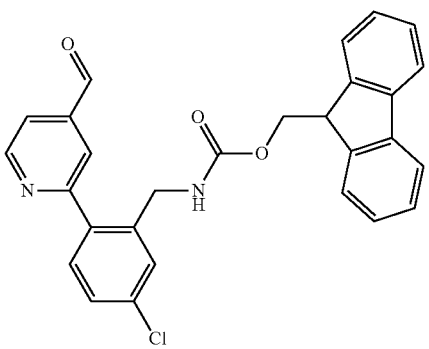 [SMILES: O=Cc1ccnc(-c2ccc(Cl)cc2CNC(=O)OCC2c3ccccc3-c3ccccc32)c1]

To a solution of n-butylmagnesium chloride 2.0M in THF (4.62 mL, 9.24 mmol, Eq: 1) diluted with dry THF (30 mL) was added at 0° C. n-BuLi 1.6M in hexanes (11.5 mL, 18.5 mmol, Eq: 2). This mixture was cooled to −70° C. A solution of 2-bromo-5-chlorobenzonitrile (2 g, 9.24 mmol, Eq: 1) in dry THF (20 mL) was added dropwise at −70° C. The reaction mixture was stirred for 30 minutes at −70° C. Freshly prepared ZnCl2 1.0M in THF (27.7 mL, 27.7 mmol, Eq: 3) was added and the reaction mixture was allowed to warm to room temperature and stirred for 1 hour at room temperature. tetrakis(triphenylphosphine)palladium(0) (534 mg, 462 µmol, Eq: 0.05) and a solution of methyl 2-bromoisonicotinate (2 g, 9.24 mmol, Eq: 1) in dry THF (20 mL) was added. The reaction mixture was stirred for 3 hours at reflux. The reaction mixture was poured on 200 mL 10% aqueous NaHCO3 solution and 100 mL EtOAc. The layers were separated. The aqueous layer was extracted a second time with 200 mL EtOAc. The organic layers were washed with 200 mL brine, dried over MgSO4, filtered and concentrated under vacuum. The residue was purified by silica gel chromatography to yield methyl 2-(4-chloro-2-cyanophenyl)pyridine-4-carboxylate as an orange solid (600 mg, 23.8%). MS (ESI): m/z=273.043 [M+H].

To a solution of LiAlH4 1M in THF (4.4 mL, 4.4 mmol, Eq: 4) diluted with dry THF (7 mL) was added at −20° C. dropwise a solution of methyl 2-(4-chloro-2-cyanophenyl)pyridine-4-carboxylate (300 mg, 1.1 mmol, Eq: 1) in dry THF (7 mL) within 30 minutes. The reaction mixture was allowed to warm to room temperature and then stirred for 1.5 hours at room temperature. The reaction mixture was poured on 30 mL saturated aqueous sodium potassium tartrate solution (containing ca. 2 mL aqueous 1N NaOH) and 30 mL EtOAc and the layers were separated. The aqueous layer was extracted a second time with 30 mL EtOAc. The organic layers were washed with 30 mL brine, dried over MgSO4, filtered and concentrated under vacuum to yield [2-[2-(aminomethyl)-4-chlorophenyl]pyridin-4-yl]methanol (260 mg, 95%). MS (ER): m/z=249.1 [M+H]+.

To a solution of [2-[2-(aminomethyl)-4-chlorophenyl]pyridin-4-yl]methanol (260 mg, 1.05 mmol, Eq: 1) in MeOH (8 mL) was added pyridine (331 mg, 337 µL, 4.18 mmol, Eq: 4) and 9-fluorenylmethyl-N-succinimidyl carbonate (423 mg, 1.25 mmol, Eq: 1.2). The suspension was stirred for 24 hours at room temperature. The reaction mixture was poured on 30 mL 10% aqueous NaHCO3 10% solution and 30 mL EtOAc and the layers were separated. The aqueous layer was extracted a second time with 30 mL EtOAc. The organic layers were extracted with 30 mL aqueous citric acid solution and washed with 30 mL brine, dried over MgSO4, filtered and concentrated under vacuum. The residue was purified by silica gel chromatography, 9H-fluoren-9-ylmethyl N-[[5-chloro-2-[4-(hydroxymethyl)pyridin-2-yl]phenyl]methyl]carbamate was obtained as a brown oil (238 mg, 48.3%). MS (ER): m/z=471.148 [M+H]+.

To a solution 9H-fluoren-9-ylmethyl N-[[5-chloro-2-[4-(hydroxymethyl)pyridin-2-yl]phenyl]methyl]carbamate (230 mg, 488 μmol, Eq: 1) in DCM (3 mL) and THF (3 mL) was added manganese(IV) oxide activated (849 mg, 9.77 mmol, Eq: 20). The reaction mixture was stirred for 3 hours at room temperature. The reaction mixture was filtered over a pad of dicalite and washed with EtOAc. The filtrate was concentrated under vacuum. The residue was purified by silica gel chromatography to yield 9H-fluoren-9-ylmethyl N-[[5-chloro-2-(4-formylpyridin-2-yl)phenyl]methyl]carbamate as a light yellow foam (96 mg, 41.9%). MS (ESI): m/z=469.132 [M+H]+.

1H NMR (600 MHz, DMSO-d6) δ ppm 10.13 (s, 1H), 8.95 (d, J=4.9 Hz, 1H), 8.02 (s, 1H), 7.89 (d, J=7.6 Hz, 2H), 7.80 (dd, J=4.9, 1.3 Hz, 2H), 7.67 (d, J=7.4 Hz, 2H), 7.53-7.58 (m, 1H), 7.47-7.51 (m, 1H), 7.46 (s, 1H), 7.41 (tJ=7.4 Hz, 2H), 7.30-7.36 (m, 2H), 4.35 (d, J=5.8 Hz, 2H), 4.29 (d, J=7.1 Hz, 2H), 4.20 (br t, J=7.1 Hz, 1H)

General Procedure for Peptide Macrocycle Synthesis

1. Solid Phase Peptide Synthesis

The tripeptide sequence was synthesized manually via state-of-the-art solid phase synthesis protocols (Fmoc-chemistry) as referenced by e.g.: Kates and Albericio, Eds., "Solid Phase Synthesis: A practical guide", Marcel Decker, New York, Basel, 2000.

As a solid support 2-Chlor-tritylchloride resin (1.6 meq/g, 100-200 mesh) was used. This resin was loaded with 0.6 eq of amino acid and 8 eq DIPEA in dry DCM overnight at RT. After extensive washing with DMF and DCM, the Fmoc-group was cleaved off with a mixture of 50% Piperidine in DCM/DMF (1:1) in DMF (freshly prepared) for 30 min at RT. After washing with DMF, DCM and MeOH the resin was dried under vacuum at RT overnight. The resin loading was determined via weight increase.

The second amino acid was coupled with 4 eq Mukaiyama-Reagent as coupling reagent, 6 eq DIPEA in DMF/DCM (1:1) overnight at RT. The resin was extensively washed with DMF and DCM and the coupling rate was controlled by a test-cleavage.

The Fmoc-group from the dipeptide was cleaved with a mixture of 50% Piperidine (25%)/DCM (25%) in DMF for maximally 5 min followed by washings with DMF and DCM. The cleavage rates were again controlled by test-cleavage.

The third amino acid was coupled using an excess of 4 eq using 4 eq HATU as coupling reagent and 6 eq DIPEA. Complete couplings were accomplished at RT for 2-4 hours with the coupling rate again controlled by a test-cleavage.

The Fmoc-group from the tripeptide was cleaved with a mixture of 20% Piperidine in DMF for 2×15-20 min at RT followed by washings with DMF and DCM (test-cleavage).

2. Reductive Amination:

Resin with tripeptide was washed with DCM, the corresponding Intermediate dissolved in a mixture of NMP/TMOF/AcOH (49.7/49.7/0.6) and the solution was added to the resin. The mixture was shaken at RT for 30 min up to 3 h, then 10 eq NaCNBH3 were added and the reaction mixture was shaken at RT overnight. Finally, the resin was washed with DMF, DCM, MeOH/DCM (1:1) and DMF.

The Fmoc-group on the tether was cleaved with a mixture of 20% Piperidine in DMF for 2×15-20 min at RT followed by washings with DMF and DCM (test-cleavage).

3. Cleavage:

A cleavage-cocktail of 20% HFIP in DCM was added to the resin and the mixture was stirred for 2 h at RT. The resin was filtered off and the solution was evaporated to dryness. The residue was dissolved in water/acetonitrile and lyophilized.

4. Cyclisation:

The obtained crude linear compound was cyclized by dissolving the powder in DMF. 1.2 eq HATU and 5eq DIPEA were added and the reaction mixture stirred at RT. Progress of the reaction was monitored by HPLC. After completion, the solvent was evaporated, the resulting residue taken up in water/acetonitrile (1:1) and lyophilized.

5. Purification:

Peptide macrocycles were purified using reversed phase high-performance liquid chromatography (RP-HPLC) using a Reprospher 100 C18-TDE column (250×20 mm, 5 um particle size) as a stationary phase and water/acetonitrile as eluent (Gradient 40-100% MeCN over 60 min). Fractions were collected and analyzed by LC/MS. Pure product samples were combined and lyophilized. Product identification was obtained via mass spectrometry.

6. Global deprotection:

Final BOC-deprotection was achieved by 50% TFA (DCM) treatment for 2 h at RT. The reaction solution was concentrated down and the residue freeze-dried to yield the deprotected product as TFA salt. All peptides were obtained as white powders with a purity >90%.

Example 1

(11S,14S,17S)-14-(4-Amino-butyl)-17-(3-aminopropyl)-11-(1H-indol-3-ylmethyl)-12-methyl-9,12,15,18-tetraaza-tricyclo[18.3.1.0*2,7]tetracosa-1(24),2(7),3,5,20,22-hexaene-10,13,16-trione

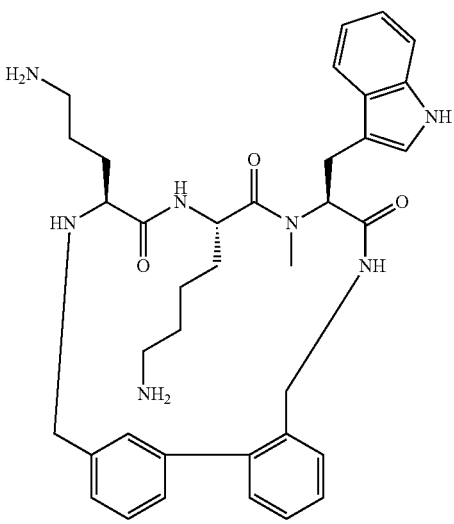 [SMILES: CN1C(=O)[C@H](CCCCN)NC(=O)[C@H](CCCN)NCc2cccc(c2)-c2ccccc2CNC(=O)[C@@H]1Cc1c[nH]c2ccccc12]

Example 1 was prepared according to the General Procedure for Peptide Macrocycle Synthesis using the following starting materials:

Amino acids:
1. Fmoc-L-NMe-Trp(Boc)-OH
2. Fmoc-L-Lys(Boc)-OH
3. Fmoc-L-Orn(Boc)-OH Tether: Intermediate 1

MS: m/z=638.38 (M+H)$^+$

Example 2

(11S,14S,17S)-14-(4-Amino-butyl)-17-(3-amino-propyl)-11-(1H-indol-3-ylmethyl)-12-methyl-3-trifluoromethyl-9,12,15,18-tetraaza-tricyclo[18.3.1.0*2,7]tetracosa-1(24),2(7),3,5,20,22-hexaene-10,13,16-trione

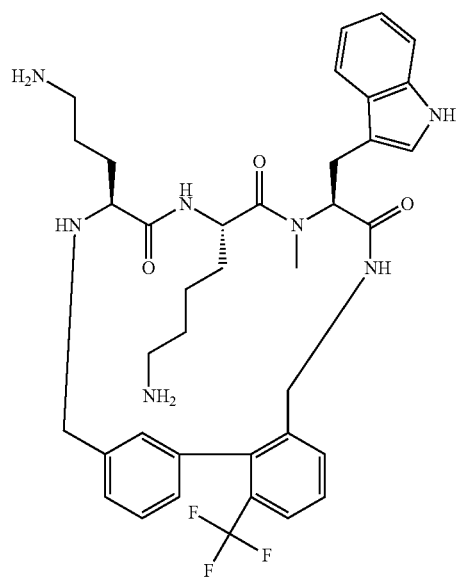 [SMILES: CN1C(=O)[C@H](CCCCN)NC(=O)[C@H](CCCN)NCc2cccc(c2)-c2c(cccc2C(F)(F)F)CNC(=O)[C@@H]1Cc1c[nH]c2ccccc12]

Example 2 was prepared according to the General Procedure for Peptide Macrocycle Synthesis using the following starting materials:

Amino acids:
1. Fmoc-L-NMe-Trp(Boc)-OH
2. Fmoc-L-Lys(Boc)-OH
3. Fmoc-L-Orn(Boc)-OH Tether: Intermediate 2

MS: m/z=706.37(M+H)$^+$

Example 3

(11S,14S,17S)-14-(4-Amino-butyl)-17-(3-amino-propyl)-11-(1H-indol-3-ylmethyl)-12-methyl-5-trifluoromethyl-9,12,15,18-tetraaza-tricyclo[18.3.1.0*2,7]tetracosa-1(24),2(7),3,5,20,22-hexaene-10,13,16-trione

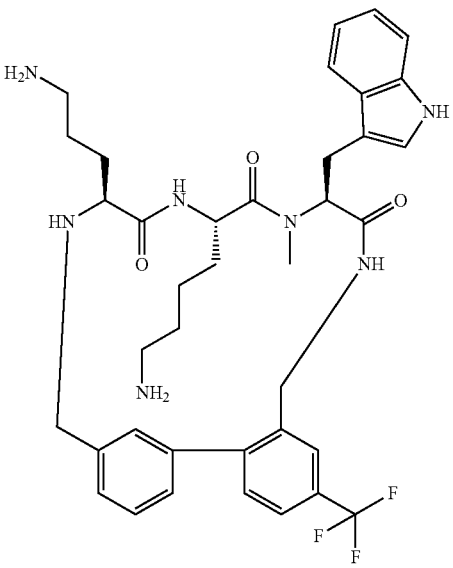 [SMILES: CN1C(=O)[C@H](CCCCN)NC(=O)[C@H](CCCN)NCc2cccc(c2)-c2ccc(C(F)(F)F)cc2CNC(=O)[C@@H]1Cc1c[nH]c2ccccc12]

Example 3 was prepared according to the General Procedure for Peptide Macrocycle Synthesis using the following starting materials:

Amino acids:
1. Fmoc-L-NMe-Trp(Boc)-OH
2. Fmoc-L-Lys(Boc)-OH
3. Fmoc-L-Orn(Boc)-OH Tether: Intermediate 3

MS: m/z=(M+H)$^+$

Example 4

(11S,14S,17S)-14-(4-Amino-butyl)-17-(3-amino-propyl)-11-(1H-indol-3-ylmethyl)-3,12-dimethyl-9,12,15,18-tetraaza-tricyclo[18.3.1.0*2,7]tetracosa-1(23),2(7),3,5,20(24),21-hexaene-10,13,16-trione

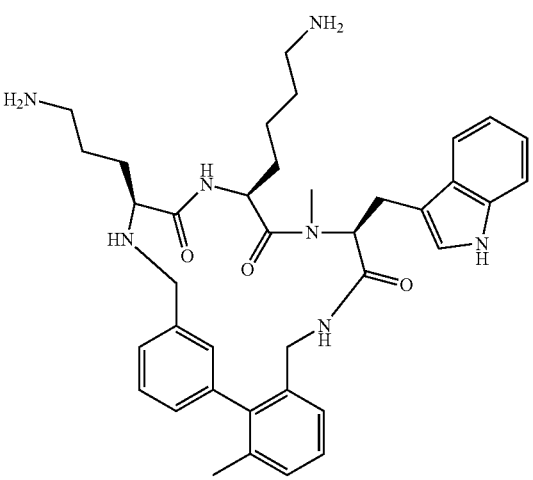 [SMILES: Cc1cccc2c1-c1cccc(c1)CN[C@@H](CCCN)C(=O)N[C@@H](CCCCN)C(=O)N(C)[C@@H](Cc1c[nH]c3ccccc13)C(=O)NC2]

Example 4 was prepared according to the General Procedure for Peptide Macrocycle Synthesis using the following starting materials:

Amino acids:
1. Fmoc-L-NMe-Trp(Boc)-OH
2. Fmoc-L-Lys(Boc)-OH
3. Fmoc-L-Orn(Boc)-OH Tether: Intermediate 4
MS: m/z=652.7 (M+H)+

Example 5

(11S,14S,17S)-14-(4-Amino-butyl)-17-(3-amino-propyl)-5-chloro-11-(1H-indol-3-ylmethyl)-12-methyl-9,12,15,18-tetraaza-tricyclo[18.3.1.0*2,7]tetracosa-1(23),2(7),3,5,20(24),21-hexaene-10,13,16-trione

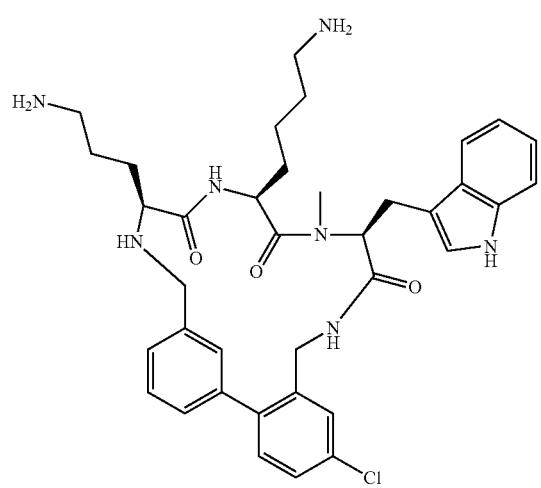 [SMILES: CN1C(=O)[C@H](CCCCN)NC(=O)[C@H](CCCN)NCc2cccc(c2)-c2ccc(Cl)cc2CNC(=O)[C@@H]1Cc1c[nH]c2ccccc12]

Example 5 was prepared according to the General Procedure for Peptide Macrocycle Synthesis using the following starting materials:

Amino acids:
1. Fmoc-L-NMe-Trp(Boc)-OH
2. Fmoc-L-Lys(Boc)-OH
3. Fmoc-L-Orn(Boc)-OH Tether: Intermediate 5
MS: m/z=672.7 (M+H)+

Example 6

(11S,14S,17S)-14-(4-Amino-butyl)-17-(3-amino-propyl)-6-chloro-11-(1H-indol-3-ylmethyl)-12-methyl-9,12,15,18-tetraaza-tricyclo[18.3.1.0*2,7]tetracosa-1(23),2(7),3,5,20(24),21-hexaene-10,13,16-trione

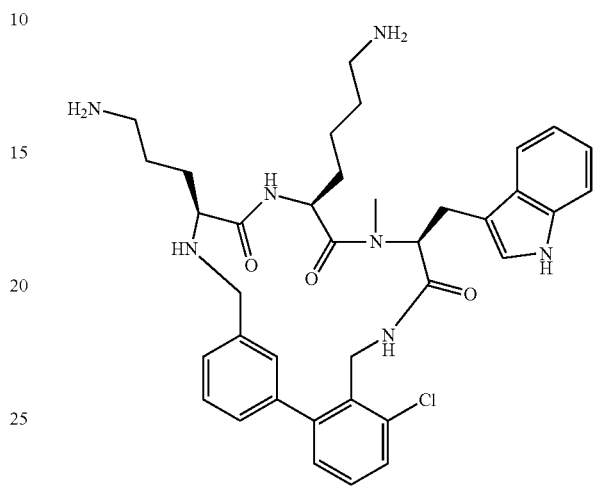

Example 6 was prepared according to the General Procedure for Peptide Macrocycle Synthesis using the following starting materials:

Amino acids:
1. Fmoc-L-NMe-Trp(Boc)-OH
2. Fmoc-L-Lys(Boc)-OH
3. Fmoc-L-Orn(Boc)-OH Tether: Intermediate 6
MS: m/z=672.6 (M+H)+

Example 7

(11S,14S,17S)-14-(4-Amino-butyl)-17-(3-amino-propyl)-11-(1H-indol-3-ylmethyl)-5,12-dimethyl-9,12,15,18-tetraaza-tricyclo[18.3.1.0*2,7]tetracosa-1(23),2(7),3,5,20(24),21-hexaene-10,13,16-trione

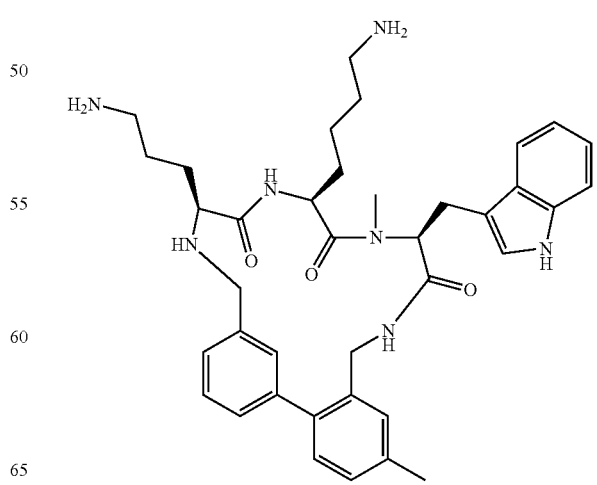

Example 7 was prepared according to the General Procedure for Peptide Macrocycle Synthesis using the following starting materials:
Amino acids:
1. Fmoc-L-NMe-Trp(Boc)-OH
2. Fmoc-L-Lys(Boc)-OH
3. Fmoc-L-Orn(Boc)-OH
Tether: Intermediate 7
MS: m/z=652.7 (M+H)$^+$ Example 8

(11S,14S,17S)-14-(4-Amino-butyl)-17-(3-amino-propyl)-11-(1H-indol-3-ylmethyl)-12-methyl-4-trifluoromethyl-9,12,15,18-tetraaza-tricyclo[18.3.1.0*2,7]tetracosa-1(24),2(7),3,5,20,22-hexaene-10,13,16-trione

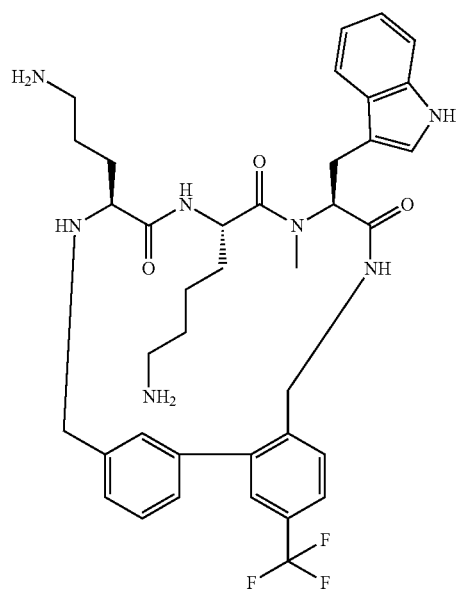 [SMILES: CN1C(=O)[C@H](CCCCN)NC(=O)[C@H](CCCN)NCc2cccc(c2)-c2cc(C(F)(F)F)ccc2CNC(=O)[C@@H]1Cc1c[nH]c2ccccc12]

Example 8 was prepared according to the General Procedure for Peptide Macrocycle Synthesis using the following starting materials:
Amino acids:
1. Fmoc-L-NMe-Trp(Boc)-OH
2. Fmoc-L-Lys(Boc)-OH
3. Fmoc-L-Orn(Boc)-OH
Tether: Intermediate 8
MS: m/z=706.37(M+H)$^+$ Example 9

(11S,14S,17S)-14-(4-Amino-butyl)-17-(3-amino-propyl)-11-(1H-indol-3-ylmethyl)-5-methoxy-12-methyl-9,12,15,18-tetraaza-tricyclo[18.3.1.0*2,7]tetracosa-1(23),2(7),3,5,20(24),21-hexaene-10,13,16-trione

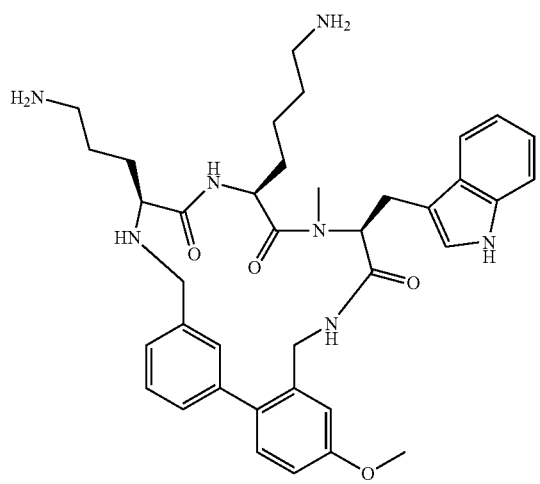 [SMILES: COc1ccc2c(c1)CNC(=O)[C@H](Cc1c[nH]c3ccccc13)N(C)C(=O)[C@H](CCCCN)NC(=O)[C@H](CCCN)NCc1cccc-2c1]

Example 9 was prepared according to the General Procedure for Peptide Macrocycle Synthesis using the following starting materials:
Amino acids:
1. Fmoc-L-NMe-Trp(Boc)-OH
2. Fmoc-L-Lys(Boc)-OH
3. Fmoc-L-Orn(Boc)-OH
Tether: Intermediate 9
MS: m/z=668.7 (M+H)$^+$ Example 10

(11S,14S,17S)-14-(4-Amino-butyl)-17-(3-amino-propyl)-24-fluoro-11-(1H-indol-3-ylmethyl)-12-methyl-9,12,15,18-tetraaza-tricyclo[18.3.1.0*2,7]tetracosa-1(23),2(7),3,5,20(24),21-hexaene-10,13,16-trione

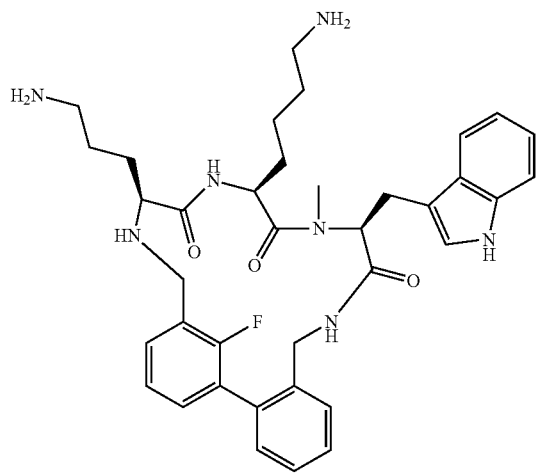 [SMILES: CN1C(=O)[C@H](CCCCN)NC(=O)[C@H](CCCN)NCc2cccc(c2F)-c2ccccc2CNC(=O)[C@@H]1Cc1c[nH]c2ccccc12]

Example 10 was prepared according to the General Procedure for Peptide Macrocycle Synthesis using the following starting materials:
Amino acids:
1. Fmoc-L-NMe-Trp(Boc)-OH
2. Fmoc-L-Lys(Boc)-OH
3. Fmoc-L-Orn(Boc)-OH
Tether: Intermediate 10
MS: m/z=656.6 (M+H)$^+$ Example 11

(11S,14S,17S)-14-(4-Amino-butyl)-17-(3-amino-propyl)-5-chloro-11-(1H-indol-3-ylmethyl)-12-methyl-9,12,15,18,23-pentaaza-tricyclo[18.3.1.0*2,7]tetracosa-1(23),2(7),3,5,20(24),21-hexaene-10,13,16-trione

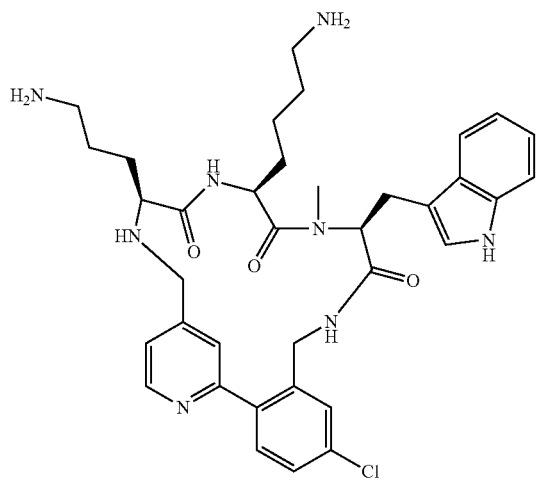 [SMILES: CN1C(=O)[C@H](CCCCN)NC(=O)[C@H](CCCN)NCc2ccnc(c2)-c2ccc(Cl)cc2CNC(=O)[C@@H]1Cc1c[nH]c2ccccc12]

Example 11 was prepared according to the General Procedure for Peptide Macrocycle Synthesis using the following starting materials:
Amino acids:
1. Fmoc-L-NMe-Trp(Boc)-OH
2. Fmoc-L-Lys(Boc)-OH
3. Fmoc-L-Orn(Boc)-OH
Tether: Intermediate 11
MS: m/z=673.34 (M+H)$^+$ Example 12

Antimicrobial Susceptibility Testing: Minimum Inhibitory Concentration (MIC) Determination The in vitro antimicrobial activity of the compounds was determined through microbroth minimum inhibitory concentration (MIC) methodology performed according to the Clinical and Laboratory Standard Institute guidelines (*CLSI-M07-A9 January* 2012. *Methods for Dilution Antimicrobial Susceptibility Tests for Bacteria That Grow Aerobically; Approved Standard Ninth Edition, Clinical and Laboratory Standards Institute, Wayne/PA, US* and the *CLSI-M*100-*S*24 *January* 2014. *Performance Standards for Antimicrobial Susceptibility Testing; Approved Standard—Fourth Informational Supplement, Clinical and Laboratory Standards Institute, Wayne/PA, US*).

The compound stock solution was freshly prepared at 10× the required top concentration for the MIC determination, i.e. at 1280 mg/L, by reconstitution of the dry compound in 50:50 water:DMSO.

Polystyrene non-treated 96 wells microtiter plates were used for preparing panel containing compound serial twofold diluted at two times the final testing concentration (e.g. range from 64 to 0.06 µg/ml) in cation adjusted Mueller Hinton broth medium (CAMHB).

Inoculum was prepared by the "direct colony suspension method". Colonies of *A. baumannii* ATCC19606 or clinical isolates were suspended in saline solution and adjusted to 0.5 McFarland, diluted 100 times in CAMHB broth and 50 µl added to each well (final concentration of cells~5×10$^{(5)}$ CFU/ml and Final volume/well of 100 µl). Microtiter plates were sealed and incubated at 35±2° C.

MICs values were read after 20 hours of incubation and recorded as the lowest concentration of the antimicrobial that inhibits more or equal to 80% of growth of the organism as detected by the unaided eye and using a microtiter plate optical density reader (OD 600 nm).

Table 1 provides the minimum inhibitory concentration (MIC) in microgram per milliliter of the compounds of present invention obtained against the *A. baumannii* strain ATCC19606.

Particular compounds of the present invention exhibit a MIC (ATCC19606)≤50 µg/ml.

More particular compounds of the present invention exhibit a MIC (ATCC19606)≤5 µg/ml.

Most particular compounds of the present invention exhibit a MIC (ATCC19606)≤1 µg/ml.

Example 13

Antimicrobial Susceptibility Testing: 50% Growth Inhibitory Concentration (IC50) Determination The in vitro antimicrobial activity of the compounds was alternatively determined according to the following procedure:

The assay used a 10-points Iso-Sensitest broth medium to measure quantitatively the in vitro activity of the compounds against *A. baumannii* ATCC17978.

Stock compounds in DMSO were serially twofold diluted (e.g. range from 50 to 0.097 µM final concentration) in 384 wells microtiter plates and inoculated with 49 µl the bacterial suspension in Iso-Sensitest medium to have a final cell concentration of ~5×10$^{(5)}$ CFU/ml in a final volume/well of 50 ul/well. Microtiter plates were incubated at 35±2° C.

Bacterial cell growth was determined with the measurement of optical density at λ=600 nm each 20 minutes over a time course of 16 h.

Growth inhibition was calculated during the logarithmic growth of the bacterial cells with determination of the concentration inhibiting 50% (IC50) and 90% (IC90) of the growth.

Table 1 provides the 50% growth inhibitory concentrations (IC50) in micromoles per liter of the compounds of present invention obtained against the *A. baumannii* strain ATCC17978.

TABLE 1

Minimum inhibitory concentration (MIC) in microgram per milliliter of the compounds of present invention obtained against *A. baumannii* strain ATCC19606 and 50% growth inhibition concentrations (IC50) in micromoles per liter of the compounds of present invention obtained against *A. baumannii* strain ATCC17978.

| Example | ATCC17978 IC50 [µg/ml] | Example | ATCC19606 MIC [µg/ml] |
|---|---|---|---|
| 1 | 11.3 | 1 | 32 |
| 2 | 5.3 | 2 | 2 |
| 3 | 0.3 | 3 | 0.5 |
| 4 | — | 4 | 32 |
| 5 | 0.4 | 5 | 4 |
| 6 | — | 6 | 32 |
| 7 | — | 7 | 1 |
| 8 | — | 8 | 4 |
| 9 | — | 9 | 4 |
| 10 | — | 10 | 16 |
| 11 | — | 11 | 32 |

The invention claimed is:

1. A compound of formula (A):

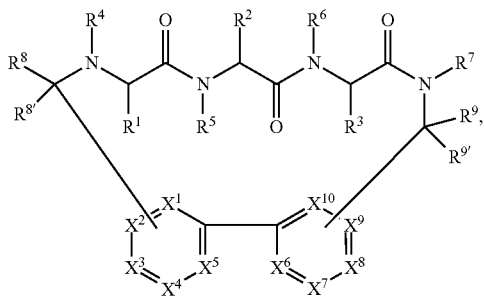

or a pharmaceutically acceptable salt thereof, wherein:
$X^1$ is C—$R^{11}$ or N;
$X^2$ is C—$R^{12}$ or N;
$X^3$ is C—$R^{13}$ or N;
$X^4$ is C—$R^{14}$ or N;
$X^5$ is C—$R^{15}$ or N, with the proviso that not more than three of $X^1$, $X^2$, $X^3$, $X^4$ and $X^5$ are N;
$X^6$ is C—$R^{16}$ or N;
$X^7$ is C—$R^{17}$ or N;
$X^8$ is C—$R^{18}$ or N;
$X^9$ is C—$R^{19}$ or N;
$X^{10}$ is C—$R^{20}$ or N, with the proviso that not more than three of $X^6$, $X^7$, $X^8$, $X^9$ and $X^{10}$ are N;
$R^{11}$, $R^{12}$, $R^{13}$, $R^{14}$, $R^{15}$, $R^{16}$, $R^{17}$, $R^{18}$, $R^{19}$ and $R^{20}$ are each individually selected from a bond, hydrogen, halogen, $C_{1-7}$-alkyl, $C_{1-7}$-haloalkyl and $C_{1-7}$-alkoxy;
$R^1$ and $R^2$ are each independently selected from hydrogen, —$C_{1-7}$-alkyl, hydroxy-$C_{1-7}$-alkyl, —$(CH_2)_m$—$NR^{20}R^{21}$, —$(CH_2)_m$—$C(O)NR^{20}R^{21}$, —$(CH_2)_m$—$CF_2$—$(CH_2)_m$—$NR^{20}R^{21}$, —$(CH_2)_m$—NH—C(O)—$(CH_2)_m$—$NR^{20}R^{21}$ or —$(CH_2)_m$—O—$(CH_2)_o$—$NR^{20}R^{21}$, —$(CH_2)_m$—NH—C(NH)—$NR^{20}R^{21}$, —$(CH_2)_m$—NH—C(O)—$OR^{21}$, —$(CH_2)_o$—$C_{3-7}$-cycloalkyl, —$(CH_2)_o$-heterocycloalkyl, —$(CH_2)_o$-heteroaryl and —$(CH_2)_o$-aryl, wherein cycloalkyl, heterocycloalkyl, heteroaryl and aryl are optionally substituted by halo, cyano, $C_{1-7}$-alkyl, $C_{1-7}$-haloalkyl, $C_{1-7}$-hydroxyalkyl, $C_{1-7}$-alkoxy or aryl;

$R^{21}$ is hydrogen;
$R^3$ is —$(CH_2)_m$-heteroaryl or —$(CH_2)_m$-heterocycloalkyl, wherein heteroaryl is optionally substituted with one or more halo, cyano, $C_{1-7}$-alkyl, $C_{1-7}$-haloalkyl, $C_{3-7}$-cycloalkyl or $C_{1-7}$-alkoxy;
$R^4$, $R^5$, $R^6$ and $R^7$ are each individually selected from hydrogen, $C_{1-7}$-alkyl, $C_{1-7}$-haloalkyl, hydroxy-$C_{1-7}$-alkyl, alkoxy-$C_{1-7}$-alkyl, —$(CH_2)_o$—$NR^{20}R^{21}$, —$(CH_2)_o$—$C_{3-7}$-cycloalkyl, —$(CH_2)_o$-heterocycloalkyl, wherein cycloalkyl and heterocycloalkyl are optionally substituted by halo, cyano, $C_{1-7}$-alkyl, $C_{1-7}$-haloalkyl, $C_{1-7}$-hydroxyalkyl, $C_{1-7}$-alkoxy or aryl;
$R^8$, $R^{8'}$, $R^9$ and $R^{9'}$ are each individually selected from hydrogen and $C_{1-3}$-alkyl;
m is 1, 2, 3, 4, 5 or 6;
n is 2, 3, 4, 5 or 6; and
o is 0, 1, 2, 3, 4, 5 or 6.

2. The compound of claim 1, wherein the compound has a structure of formula (Ia):

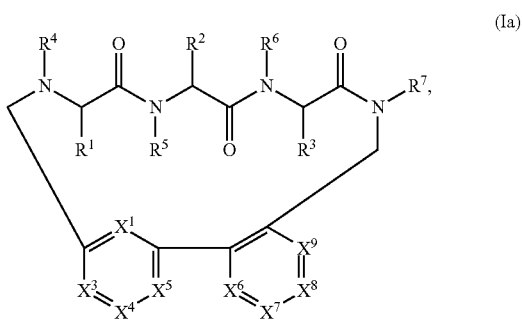

or a pharmaceutically acceptable salt thereof, wherein:
$X^1$ is C—$R^{11}$ or N;
$X^3$ is C—$R^{13}$ or N;
$X^4$ is C—$R^{14}$ or N;
$X^5$ is C—$R^{15}$ or N, with the proviso that not more than one of $X^1$, $X^3$, $X^4$ and $X^5$ is N;
$X^6$ is C—$R^{16}$ or N;
$X^7$ is C—$R^{17}$ or N;
$X^8$ is C—$R^{18}$ or N;
$X^9$ is C—$R^{19}$ or N, with the proviso that not more than one of $X^5$, $X^6$, $X^7$, $X^8$ and $X^9$ is N;
$R^{11}$, $R^{13}$, $R^{14}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy;
$R^1$ is $C_{1-7}$-alkyl, —$(CH_2)_m$—$NH_2$ or —$(CH_2)_m$—O—$(CH_2)_n$—$NH_2$;
$R^2$ is —$C_{1-7}$-alkyl, —$(CH_2)_m$—$NH_2$ or —$(CH_2)_m$—O—$(CH_2)_n$—$NH_2$;
$R^3$ is —$(CH_2)_m$-heteroaryl optionally substituted with one or more halo, $C_{1-7}$-alkyl, $C_{1-7}$-haloalkyl or $C_{1-7}$-alkoxy;
$R^4$, $R^5$, $R^6$ and $R^7$ are each individually selected from hydrogen and $C_{1-3}$-alkyl;
m is 1, 2, 3, 4, 5 or 6; and
n is 2, 3, 4, 5 or 6.

3. The compound of claim 1, wherein the compound has a structure of formula (Ia'):

(Ia')

or a pharmaceutically acceptable salt thereof, wherein:
$X^1$ is C—$R^{11}$ or N;
$X^3$ is C—$R^{13}$ or N;
$X^4$ is C—$R^{14}$ or N;
$X^5$ is C—$R^{15}$ or N, with the proviso that not more than one of $X^1$, $X^3$, $X^4$ and $X^5$ is N;
$X^6$ is C—$R^{16}$ or N;
$X^7$ is C—$R^{17}$ or N;
$X^8$ is C—$R^{18}$ or N;
$X^9$ is C—$R^{19}$ or N, with the proviso that not more than one of $X^5$, $X^6$, $X^7$, $X^8$ and $X^9$ is N;
$R^{11}$, $R^{13}$, $R^{14}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy;
$R^1$ is —$(CH_2)_m$—$NH_2$;
$R^2$ is —$(CH_2)_m$—$NH_2$;
$R^3$ is —$(CH_2)_m$-heteroaryl optionally substituted with one or more halo, $C_{1-7}$-alkyl, $C_{1-7}$-haloalkyl or $C_{1-7}$-alkoxy; and
m is 1, 2 or 3.

4. The compound of claim 1, wherein the compound has a structure of formula (Ia''):

(Ia'')

or a pharmaceutically acceptable salt thereof, wherein:
$X^1$ is C—$R^{11}$ or N;
$X^3$ is C—$R^{13}$ or N;
$X^4$ is C—$R^{14}$ or N;
$X^5$ is C—$R^{15}$ or N, with the proviso that not more than one of $X^1$, $X^3$, $X^4$ and $X^5$ is N;
$X^6$ is C—$R^{16}$ or N;
$X^7$ is C—$R^{17}$ or N;
$X^8$ is C—$R^{18}$ or N;
$X^9$ is C—$R^{19}$ or N, with the proviso that not more than one of $X^5$, $X^6$, $X^7$, $X^8$ and $X^9$ is N;
and
$R^{11}$, $R^{13}$, $R^{14}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy.

5. The compound of claim 1, wherein the compound has a structure of formula (Ia'''):

(Ia''')

or a pharmaceutically acceptable salt thereof, wherein:
$X^1$ is C—$R^{11}$ or N;
$X^5$ is C—$R^{15}$ or N, with the proviso that not more than one of $X^1$ and $X^5$ is N;
$X^6$ is C—$R^{16}$ or N;
$X^7$ is C—$R^{17}$ or N;
$X^8$ is C—$R^{18}$ or N;
$X^9$ is C—$R^{19}$ or N, with the proviso that not more than one of $X^5$, $X^6$, $X^7$, $X^8$ and $X^9$ is N;
and
$R^{11}$, $R^{15}$, $R^{16}$, $R^{17}$, $R^{18}$ and $R^{19}$ are each individually selected from hydrogen, halogen, $C_{1-7}$-alkyl, $C_{1-7}$-haloalkyl and $C_{1-7}$-alkoxy.

6. The compound of claim 5, wherein:
$X^1$ is CH;
$X^5$ is CH;
$X^6$ is C—$R^{16}$;
$X^7$ is C—$R^{17}$;
$X^8$ is C—$R^{18}$;
$X^9$ is C—$R^{19}$; and
$R^{16}$, $R^{17}$, $R^{18}$, $R^{19}$ are each individually selected from hydrogen, halogen, $C_{1-3}$-alkyl, $C_{1-3}$-haloalkyl and $C_{1-3}$-alkoxy.

7. The compound of claim 1, wherein the compound is selected from the group consisting of:
(11S,14S,17S)-14-(4-Amino-butyl)-17-(3-amino-propyl)-11-(1H-indol-3-ylmethyl)-12-methyl-9,12,15,18-tetraaza-tricyclo[18.3.1.0*2,7*]tetracosa-1(24),2(7),3,5,20,22-hexaene-10,13,16-trione;
(11S,14S,17S)-14-(4-Amino-butyl)-17-(3-amino-propyl)-11-(1H-indol-3-ylmethyl)-12-methyl-3-trifluoromethyl-9,12,15,18-tetraaza-tricyclo[18.3.1.0*2,7*] tetracosa-1(24),2(7),3,5,20,22-hexaene-10,13,16-trione;
(11S,14S,17S)-14-(4-Amino-butyl)-17-(3-amino-propyl)-11-(1H-indol-3-ylmethyl)-12-methyl-5-trifluoromethyl-9,12,15,18-tetraaza-tricyclo[18.3.1.0*2,7*]
tetracosa-1(24),2(7),3,5,20,22-hexaene-10,13,16-
trione;

(11S,14S,17S)-14-(4-Amino-butyl)-17-(3-amino-propyl)-11-(1H-indol-3-ylmethyl)-3,12-dimethyl-9,12,15,18-tetraaza-tricyclo[18.3.1.0*2,7*]tetracosa-1(23),2(7),3,5,20(24),21-hexaene-10,13,16-trione;

(11S,14S,17S)-14-(4-Amino-butyl)-17-(3-amino-propyl)-5-chloro-11-(1H-indol-3-ylmethyl)-12-methyl-9,12,15,18-tetraaza-tricyclo[18.3.1.0*2,7*]tetracosa-1(23),2(7),3,5,20(24),21-hexaene-10,13,16-trione;

(11S,14S,17S)-14-(4-Amino-butyl)-17-(3-amino-propyl)-6-chloro-11-(1H-indol-3-ylmethyl)-12-methyl-9,12,15,18-tetraaza-tricyclo[18.3.1.0*2,7*]tetracosa-1(23),2(7),3,5,20(24),21-hexaene-10,13,16-trione;

(11S,14S,17S)-14-(4-Amino-butyl)-17-(3-amino-propyl)-11-(1H-indol-3-ylmethyl)-5,12-dimethyl-9,12,15,18-tetraaza-tricyclo[18.3.1.0*2,7*]tetracosa-1(23),2(7),3,5,20(24),21-hexaene-10,13,16-trione;

(11S,14S,17S)-14-(4-Amino-butyl)-17-(3-amino-propyl)-11-(1H-indol-3-ylmethyl)-12-methyl-4-trifluoromethyl-9,12,15,18-tetraaza-tricyclo[18.3.1.0*2,7*]tetracosa-1(24),2(7),3,5,20,22-hexaene-10,13,16-trione;

(11S,14S,17S)-14-(4-Amino-butyl)-17-(3-amino-propyl)-11-(1H-indol-3-ylmethyl)-5-methoxy-12-methyl-9,12,15,18-tetraaza-tricyclo[18.3.1.0*2,7*]tetracosa-1(23),2(7),3,5,20(24),21-hexaene-10,13,16-trione;

(11S,14S,17S)-14-(4-Amino-butyl)-17-(3-amino-propyl)-24-fluoro-11-(1H-indol-3-ylmethyl)-12-methyl-9,12,15,18-tetraaza-tricyclo[18.3.1.0*2,7*]tetracosa-1(23),2(7),3,5,20(24),21-hexaene-10,13,16-trione; and (11S,14S,17S)-14-(4-Amino-butyl)-17-(3-amino-propyl)-5-chloro-11-(1H-indol-3-ylmethyl)-12-methyl-9,12,15,18,23-pentaaza-tricyclo[18.3.1.0*2,7*]tetracosa-1(23),2(7),3,5,20(24),21-hexaene-10,13,16-trione;

or a pharmaceutically acceptable salt thereof.

8. A process for the manufacture of a compound of claim 1, or a pharmaceutically acceptable salt thereof, the process comprising the steps of:

a) reacting a compound of formula (III) with a compound of formula (IV) in the presence of sodium cyanoborohydride (NaCNBH$_3$) to provide a compound of formula (II):

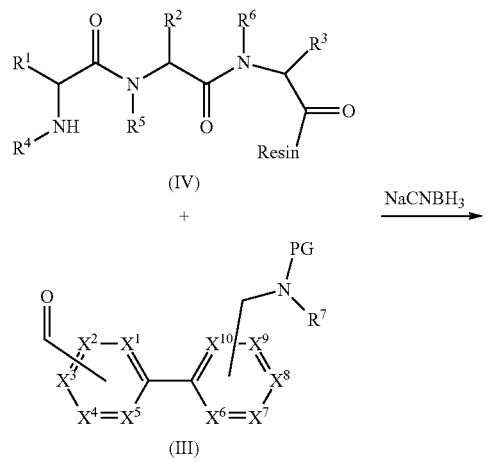

(IV)

+

NaCNBH$_3$ →

(III)

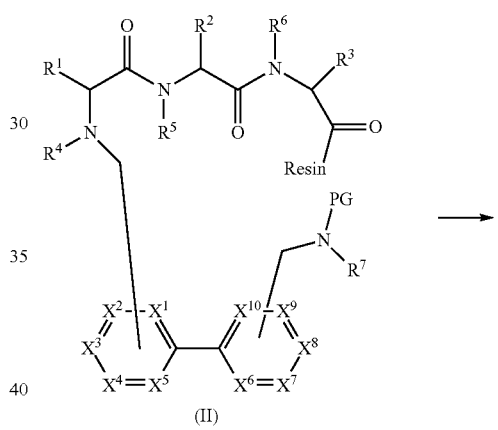

(II)

b) cleaving off the protecting group (PG) and the resin from the compound of formula (II); and c) cyclizing the cleaved compound of formula (II) in the presence of HATU and a Hünig's base to provide a compound of formula (I):

(II)

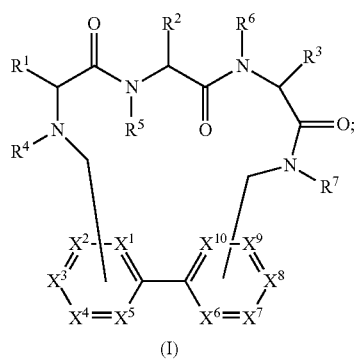

(I)

wherein R$^1$, R$^2$, R$^3$, R$^4$, R$^5$, R$^6$, R$^7$, X$^1$, X$^2$, X$^3$, X$^4$, X$^5$, X$^6$, X$^7$, X$^8$, X$^9$ and X$^{10}$ are as defined in claim 1.

9. A compound obtained by a process according to claim 8.

10. A pharmaceutical composition comprising a compound of claim 7, or a pharmaceutically acceptable salt thereof, and one or more pharmaceutically acceptable excipients.

11. A method for the treatment of infections and resulting diseases caused by *Acinetobacter baumannii*, the method comprising administering a compound of claim 7 to a human being or animal in need thereof.

* * * * *